US010821055B2

(12) United States Patent
Becker

(10) Patent No.: US 10,821,055 B2
(45) Date of Patent: Nov. 3, 2020

(54) AROMATIC PACIFIER ASSEMBLY

(71) Applicant: Stephenie Becker, Madison, AL (US)

(72) Inventor: Stephenie Becker, Madison, AL (US)

( * ) Notice: Subject to any disclaimer, the term of this patent is extended or adjusted under 35 U.S.C. 154(b) by 0 days.

(21) Appl. No.: 16/442,543

(22) Filed: Jun. 16, 2019

(65) Prior Publication Data

US 2019/0298618 A1 Oct. 3, 2019

Related U.S. Application Data

(63) Continuation-in-part of application No. 15/792,424, filed on Oct. 24, 2017.

(60) Provisional application No. 62/413,889, filed on Oct. 27, 2016.

(51) Int. Cl.
*A61J 17/00* (2006.01)
*A61L 9/014* (2006.01)
*A61J 7/00* (2006.01)

(52) U.S. Cl.
CPC ............. *A61J 17/00* (2013.01); *A61J 7/0053* (2013.01); *A61L 9/014* (2013.01); *A61L 2209/22* (2013.01)

(58) Field of Classification Search
CPC ............ A61M 21/02; A61M 2021/0016; A61J 17/001; A61J 17/008; A61J 17/00; A61J 17/006; A61J 7/0053; C11B 9/00; A61K 35/00; A61L 9/014; A61L 2209/22
USPC .................................................. 606/234, 236
See application file for complete search history.

(56) References Cited

U.S. PATENT DOCUMENTS

| | | | | |
|---|---|---|---|---|
| 3,656,647 A | * | 4/1972 | Swinn ................. | B65D 50/061 215/208 |
| 4,749,093 A | * | 6/1988 | Trick .................... | B65D 41/06 116/308 |
| 5,147,053 A | * | 9/1992 | Friedenthal .......... | B65D 50/046 215/201 |
| 5,579,933 A | * | 12/1996 | Hofmann ............. | B65D 47/283 206/536 |
| 5,620,462 A | * | 4/1997 | Valenti ................. | A61J 17/006 215/11.1 |
| 5,699,922 A | * | 12/1997 | Harding ............. | B65D 41/0478 215/201 |
| 5,947,345 A | * | 9/1999 | Hofmann ............. | B65D 50/043 221/154 |
| 6,482,225 B1 | * | 11/2002 | Bingham ............. | A61M 15/00 606/234 |
| 6,557,548 B1 | * | 5/2003 | Dickson ............... | A61M 15/00 128/200.24 |
| 2004/0044367 A1 | * | 3/2004 | Yancy ................ | B65D 81/3272 606/234 |
| 2005/0214386 A1 | * | 9/2005 | Shaheen ............... | A61K 33/00 424/661 |
| 2006/0155331 A1 | * | 7/2006 | Bohmer ............... | A61J 17/006 606/234 |

(Continued)

*Primary Examiner* — Amy R Weisberg
(74) *Attorney, Agent, or Firm* — Jacob Ong; Ongs Law Firm, PLLC

(57) ABSTRACT

An aromatic pacifier assembly for an infant gives off a predetermined scent by evaporation of volatile essential oils or similar substances. The aroma may be, for example, mint, menthol or eucalyptus, which may help relieve nasal congestion. The aromatic pacifier assembly is constructed to prevent evaporation of the essential oil before activation, so that the nipple does not become contaminated with a flavor the infant may find unpalatable, and so that the oil is conserved until it is desired to administer it to the infant.

3 Claims, 29 Drawing Sheets

(56) References Cited

U.S. PATENT DOCUMENTS

| | | | | |
|---|---|---|---|---|
| 2007/0021783 A1* | 1/2007 | Viana | ............. | A61M 15/08 |
| | | | | 606/234 |
| 2012/0022446 A1* | 1/2012 | Desai | ............. | A61J 7/0053 |
| | | | | 604/77 |
| 2012/0144556 A1* | 6/2012 | Fiebel | ............. | A41D 13/11 |
| | | | | 2/206 |
| 2015/0108239 A1* | 4/2015 | Bourne | ........... | B60H 3/0028 |
| | | | | 239/6 |
| 2016/0031605 A1* | 2/2016 | Bean | ............ | B65D 25/54 |
| | | | | 206/1.5 |
| 2018/0333336 A1* | 11/2018 | Walker | .......... | A61J 17/006 |
| 2018/0369091 A1* | 12/2018 | Avshalomov | ..... | A61K 36/185 |

* cited by examiner

AROMATIC PACIFIER ASSEMBLY

CROSS-REFERENCE TO RELATED APPLICATIONS

This application claims priority to U.S. Nonprovisional patent application Ser. No. 15/792,424, filed on Oct. 24, 2017; U.S. Nonprovisional patent application Ser. No. 15/792,424 claims priority to U.S. Provisional Patent Application No. 62/413,889 filed 27 Oct. 2016. The disclosure of those applications are specifically incorporated by reference herein for all that it discloses and teaches.

TECHNICAL FIELD

The invention relates to infant and baby products and to the field of devices that may safely be placed in a baby's mouth. More specifically, the invention relates to an aroma emitting pacifier that can be placed in the mouth of an infant or baby.

BACKGROUND

The presence of a soft but relatively impervious object that can be retained in a baby's mouth without the danger of inhalation or swallowing may have a calming or pacifying effect on the baby. Such devices are thereby often referred to as pacifiers. Since their introduction, such devices have been improved somewhat in regards to safety but little else has been improved.

As pacifiers are already something that a busy parent is used to ensuring is brought along with, or kept in close proximity to, a baby, introducing an additional functionality within the pacifier can simplify the parent's caretaking requirements. Furthermore, if that additional functionality is difficult to accomplish in any other way, then the enhanced functionality of such a pacifier is particularly valuable.

One such need is for aroma dispensing devices to help babies who are sick or otherwise need to inhale vapors/scents. There are a multitude of vaporizers and humidifiers that attempt to dispense aromas; however, they are often bulky items that are inconvenient when traveling and that impact the environment of the entire room rather than dispensing the vapor/aroma just for the baby.

What is needed is a pacifier device that has the additional functionality of dispensing an aroma. Such a device should remain sterile and not introduce any potentially unsanitary conditions. Additionally, it is important that the aroma portion of the pacifier not change the flavor or taste of the nipple portion, as a baby may refuse to utilize a pacifier that has such a modified nipple. Furthermore, the device must be simple to purchase and use, as an already busy parent does not have time to deal with multi-part pacifiers that can come apart, need refilling, or otherwise overly complicate what should remain a relatively simple and effective baby product. A need exists for a device and method of placing a sterile nipple into the mouth of a user, without substantially disrupting the efficacy of the aromatic compounds found in essential oils.

BRIEF SUMMARY

One embodiment of the present invention comprises an aroma emitting pacifier having a mouth guard, a pull ring, a housing, an aroma emitter, and a nipple. The mouth guard is sized large enough to keep the baby from fitting the entire pacifier in his or her mouth (to ensure the pacifier does not become a choking hazard, be swallowed, etc.). A pull ring may attach to the mouth guard so that either baby or parent can grasp the pull ring and maneuver the pacifier. Additionally, a short retention strap or line may be affixed to the pull ring and a nearby object so that if the pacifier is dropped, it does not fall all the way to the ground and become lost or soiled.

A cartridge assembly may be attached to a housing. Attached on the bottom side of the mouth guard may be a nipple that is designed to be placed within the mouth of the baby.

The cartridge assembly may be designed to include a repository for an aromatic substance such as medicinal vapor rub(s), fabric soaked in aromatic liquid(s), gel bulbs containing aromatic substance(s), etc. The vents of the aroma cavity may be covered by a seal which may be removed when the parent wishes to configure the pacifier to emit the aroma contained in an otherwise unsealed manner within the aroma cavity. Since the baby's nose may be in close proximity to the pacifier while the pacifier is being used, relatively small amounts of aroma substance(s) can produce relatively large effects without requiring the air in the entire room to be modified. Once the pacifier is no longer emitting significant amounts aroma(s), it can be disposed of and a new aroma emitting pacifier may be used in its place. In some embodiments, a separate sealed aroma containing cartridge may be provided as a replacement unit. The spent cartridge may be removed and discarded, and a fresh cartridge installed for future use.

"Coupled to" means linked together, connected, joined, fastened to, or secured to, and "coupled to" includes an indirect attachment. "Unremovably coupled to" means "unremovably fastened to" or "unremovably secured to." "Decoupled" means "unfastened" or "unsecured."

"Number" refers to one or more. A number of teeth could refer to a single tooth or two or more teeth.

BRIEF DESCRIPTION OF THE DRAWINGS

A more particular description of the invention briefly described above is made below by reference to specific examples. Several examples are depicted in drawings included with this application. An example is presented to illustrate, but not restrict, the invention.

FIG. 2C illustrates an exploded view of an aromatic pacifier assembly according to one example of the principles described herein.

DETAILED DESCRIPTION

Figure 1A:
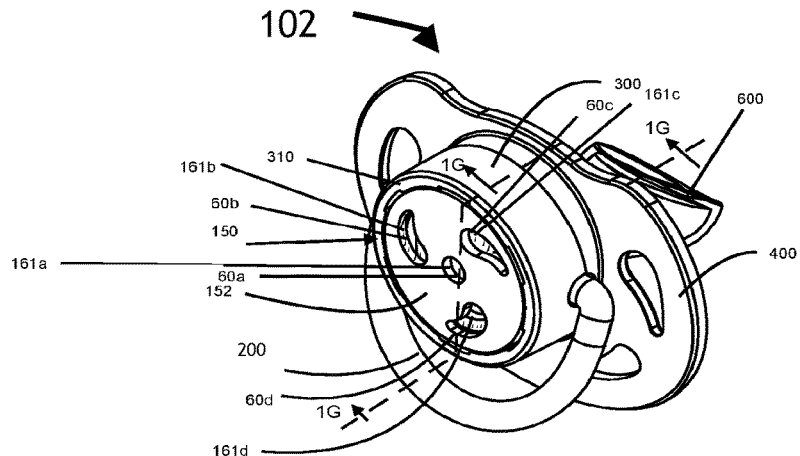
FIG. 1A illustrates a perspective view of an aromatic pacifier assembly according to one example of the principles described herein.

A detailed description of the claimed invention is provided below by example, with reference to examples in the appended figures. Those of skill in the art will recognize that the components and steps of the invention as described by example in the figures below could be arranged and designed in a wide variety of different configurations, without departing from the substance of the claimed invention. Thus, the detailed description of the examples in the figures is merely representative of an example of the invention and is not intended to limit the scope of the invention as claimed.

In some instances, numerical values are used to describe features such as temperature. Though precise numbers are used, one of skill in the art recognizes that small variations in the precisely stated values do not substantially alter the function of the feature being described. In some cases, a variation of up to 500% of the stated value does not alter the function of the feature. Thus, unless otherwise stated, precisely stated values should be read as the stated number, plus or minus a standard variation common and acceptable in the art.

The mouth guard may be sized large enough to keep the baby from fitting the entire pacifier in his or her mouth. This is desirable because if the pacifier could fit within the baby's mouth, it would become a choking hazard, could be swallowed, etc. There may be a number of air ports in the mouth guard illustrated in FIG. 1. These may provide attachment points for retention straps/strings, allow the skin that is underneath the mouth guard (when it is in use) to breathe, allow air to pass through the mouth guard, etc. In other embodiments the number, size, shape, and location of these air ports can vary or be non-existent.

An additional attachment point for a strap or retention string can be provided by the pull ring. A retention strap/line/string can be affixed to the pull ring and a nearby object so that if the pacifier is dropped, it does not fall all the way to the ground and become lost or soiled. Although not strictly necessary, the pull ring is a useful feature on the aroma emitting pacifier that can be used by either the baby or the parent to grasp and maneuver the pacifier.

The cartridge assembly may be designed to include a repository for an aromatic substance such as medicinal vapor rub(s), fabric soaked in aromatic liquid(s), gel bulbs containing aromatic substance(s), etc. Other materials that can be doused with aromatic substances include wood chips, cotton balls, strings, sponges, and any other suitable material that can initially retain and then release aromatic substances over time.

A variety of different aromatic substances may be used in an aroma emitting pacifier according to an embodiment of the invention. These substances may be non-toxic and have at least a moderate degree of volatility so that they evaporate when the seal of the aroma emitter is broken to activate the pacifier. Embodiments comprising one or more of the following substances are specifically contemplated: lavender, orange, lemon, eucalyptus, peppermint, rosemary, almond oil, coconut oil, camphor, cedar, menthol, tea tree oil, vanilla, chamomile, and cannabis. These may be pure essential oils, tinctures prepared from oils and alcohols, or other similar forms where the aromatic substance evaporates when a substantially-airtight seal is broken or removed.

The cartridge assembly may be initially sealed so that the aromas do not pervade the entire aroma emitting pacifier such that the nipple becomes flavored and the baby rejects it. Instead, the aroma emitter may contain the aroma(s) until activated by the parent just prior to giving the pacifier to the baby. Activation can be accomplished by removing a sticker or other sealant member from vents of the cartridge assembly. In other embodiments the cartridge assembly is not pre-assembled but comes as a packaged outer cartridge and a packaged inner cartridge, and the absorbent material having aromatic compounds may be packaged separately and a user may then insert the absorbent material with the aromatic compounds onto the inner surface of the inner cartridge structure or the inner surface of the outer cartridge structure and then couple the cartridge structure to the outer cartridge structure, by interlocking the teeth of the outer cartridge structure with the teeth of the inner cartridge structure, so as to form a cartridge assembly. In other embodiments, other release (activation) mechanisms are contemplated. A seal between the aroma substance and the activation button can comprise a foil, plastic, paper, rubber, silicon, gel or similar type of material (or combination) that is glued onto, melted in place, ultrasonically welded to, or otherwise affixed over vents of the outer cartridge structure. The rate of release (e.g., by evaporation) of the aromatic substance may be controlled by providing a labyrinthine channel through which the aromatic substance must travel to exit the cavity. The length and cross-section of this channel may be adjusted to account for the volatility of the aromatic substance, the quantity of substance in the chamber or cavity, and the length of time over which the aroma emitting pacifier is desired to operate.

Once the aroma(s) are released, they then travel from the aroma cavity, through aroma vents, and out of the aroma emitting pacifier. Since the baby's nose is in close proximity to the pacifier while the pacifier is being used, relatively small amounts of aroma substance(s) can produce relatively large effects without requiring the air in the entire room to be filled with aroma. Once the pacifier is no longer emitting significant amounts of aroma(s), the old aroma emitting pacifier can be disposed of and a new aroma emitting pacifier can be activated and used in its pace. In embodiments with a replaceable aroma cartridge, the spent cartridge can be removed and replaced with a new one.

Attached on the bottom side of the mouth guard is a nipple that is designed to be placed within the mouth of the baby. While the baby is sucking on and/or gumming the nipple, the aroma emitting pacifier may be constantly releasing aroma(s) in close proximity to the baby's nose and mouth. Although designed to be inhaled by the nose, when the nose is plugged and/or the baby is breathing through his or her mouth, the aromas emitted by the aroma emitting pacifier can be inhaled through the mouth as well.

Referring to FIG. 1A, an aromatic pacifier assembly is disclosed; the aromatic pacifier assembly may have a main assembly 102; the main assembly 102 may have a nipple 600, a mouth guard 400, and a housing 300 coupled to the mouth guard 400; and, a cartridge assembly 150. The cartridge assembly 150 may have an outer cartridge structure 152 and an inner cartridge structure 154. The outer cartridge structure 152 and the inner cartridge structure 154 may be undetachably attachable to each other via interlocking, flexible teeth. An absorbent material 356 be infused with an amount of aromatic compounds, essential oils, or other therapeutic scent-emitting substance; the absorbent material 356 may be disposed within the cartridge assembly 150 such that, when vents are exposed, the aromatic compounds are emitted from the cartridge assembly and may enter through a nostril of a user, such as an infant.

Referring to FIG. 1, the outer cartridge structure 152 of the aromatic pacifier assembly 101 may further include a plurality of vent areas 60a, 60b, 60c, 60d; the plurality of vent areas may each individually define a vent 161a, 161b, 161c, 161d. The aromatic pacifier assembly 101 may further have a pull ring 200 coupled to the housing 300; the inner cartridge structure 154 may also have an elliptical base 183.

Referring to FIG. 1, the aromatic pacifier assembly 101 may have at least one of the vent areas 60a that is elliptical, and wherein at least one of the vent areas 161b is generally comma-shaped. For purposes of this disclosure, comma-shaped means having an arc that is adjacent to a concave portion, which is adjacent to a convex portion.

Figure 1B:
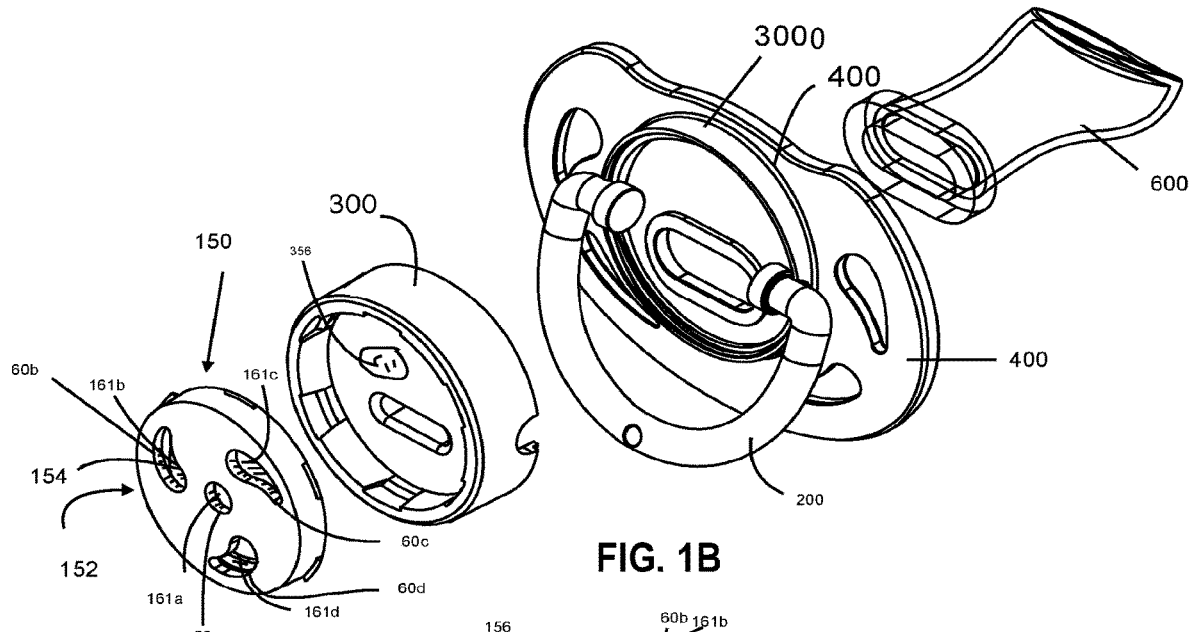
FIG. 1B illustrates an exploded view of an aromatic pacifier assembly according to one example of the principles described herein.
Figure 1C:
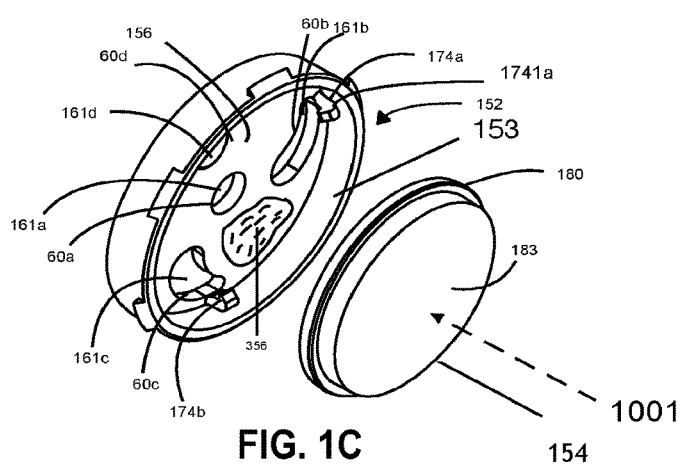
FIG. 1C illustrates a perspective exploded view of a cartridge assembly according to one example of the principles described herein.

Referring to FIG. 1, FIG. 1B, and FIG. 1C, the outer cartridge structure 152 of the aromatic pacifier assembly 101 of claim 1 may have an outer face 155 and an inner face 156; a flexible locking hook 174a may be coupled to the inner face 156. Flexible locking hook 174a may have a hooking flange 1741a.

Figure 1D:
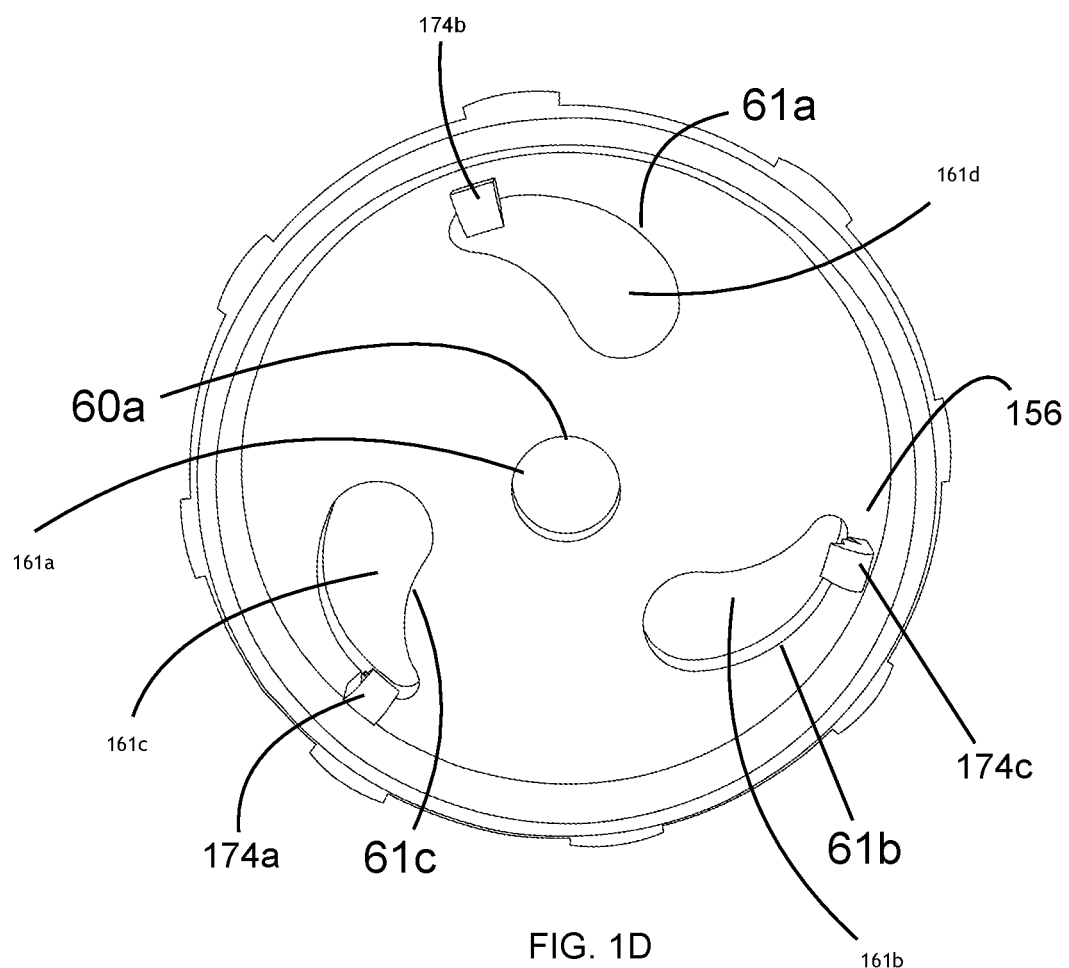
FIG. 1D illustrates a back view of an inner surface of an outer cartridge structure according to one example of the principles described herein.
Figure 1E:
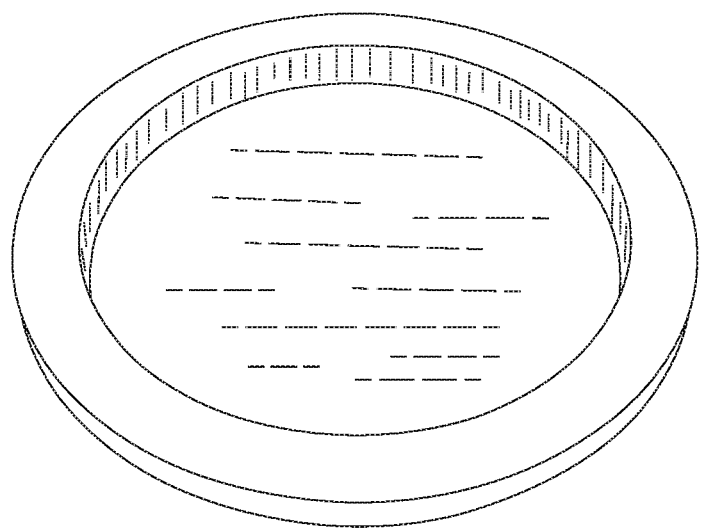
FIG. 1E illustrates a perspective view of an inner cartridge structure according to one example of the principles described herein.
Figure 1F:
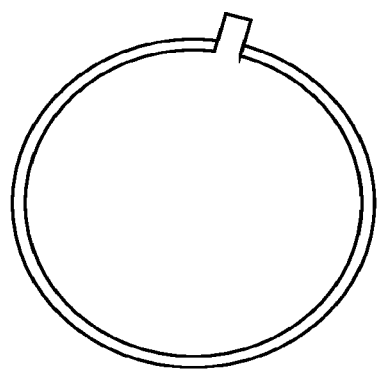
FIG. 1F illustrates a front view of an embodiment of a cartridge assembly detachably coupled to a sticker.
Figure 1G:
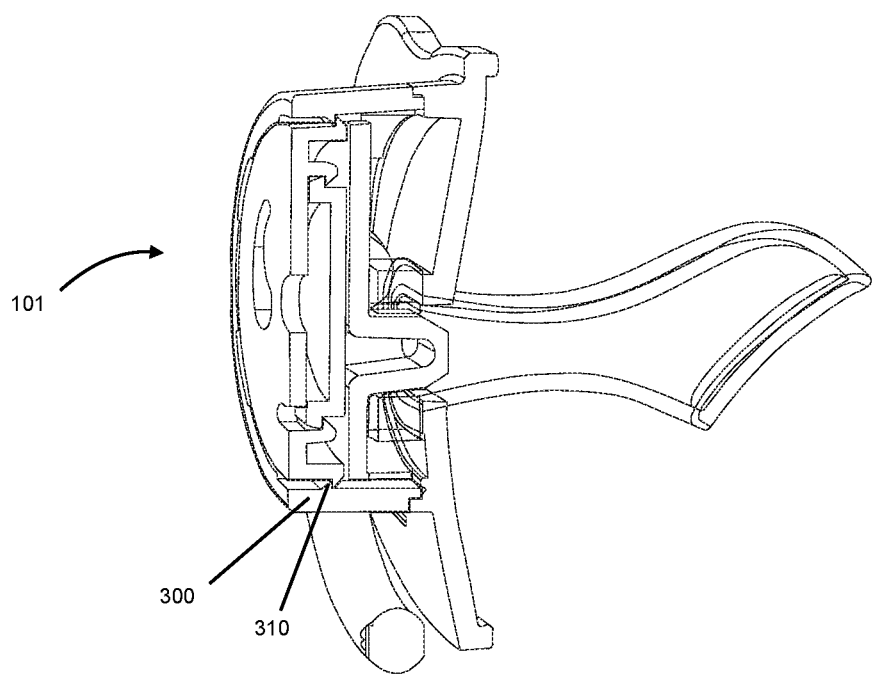
FIG. 1G illustrates a cross-sectional view of an embodiment of an aromatic pacifier assembly, see FIG. 1A for a depiction of the cross-sectional plane.

Referring to FIG. 1F, a plurality of vent areas 60a, 60b, 60c, 60d of an aromatic pacifier assembly 101 may be detachably coupled to a sticker 157. The sticker may have a back side that has an adhesive.

Figure 2A:
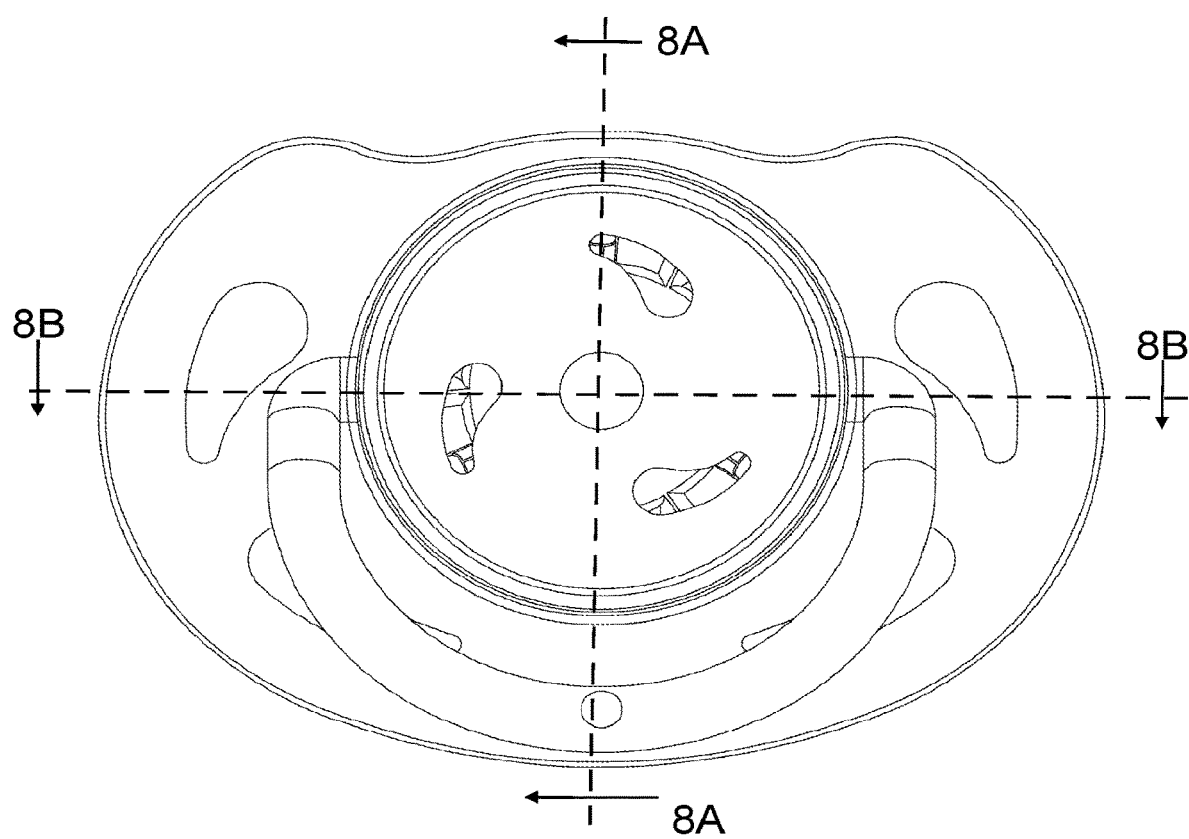
FIG. 2A illustrates a front view of an aromatic pacifier assembly according to one example of the principles described therein
Figure 2B:
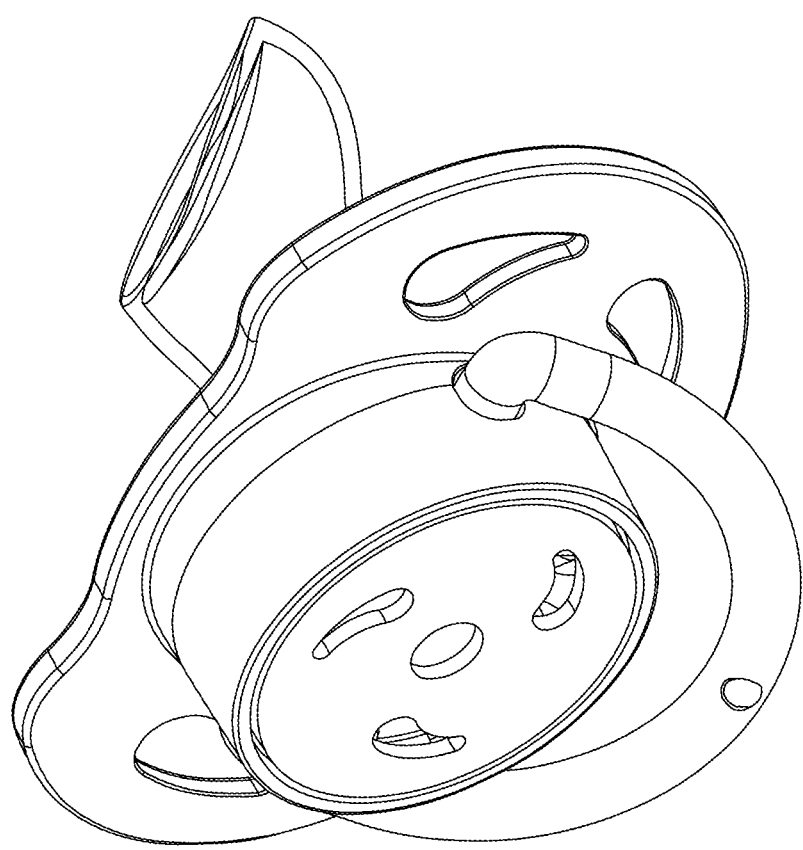
FIG. 2B illustrates a perspective view of an aromatic pacifier assembly according to one example of the principles described herein.
Figure 3A:
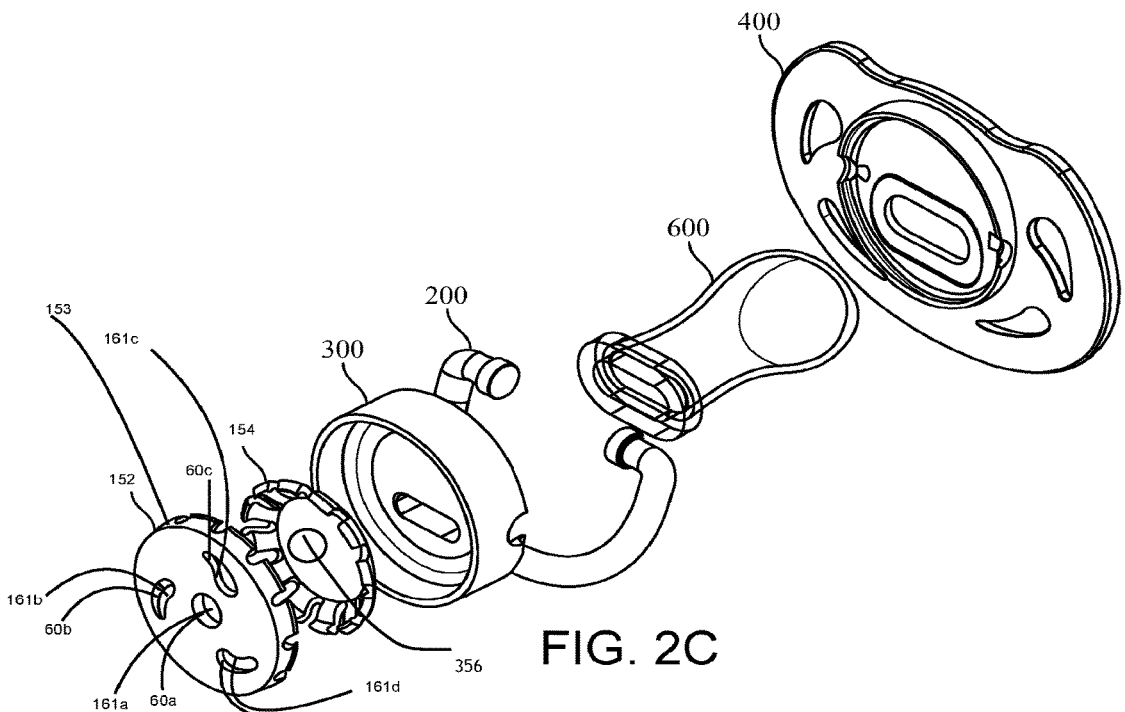
FIG. 3A illustrates a perspective view of a pull ring according to one example of the principles described herein.
Figure 3A:
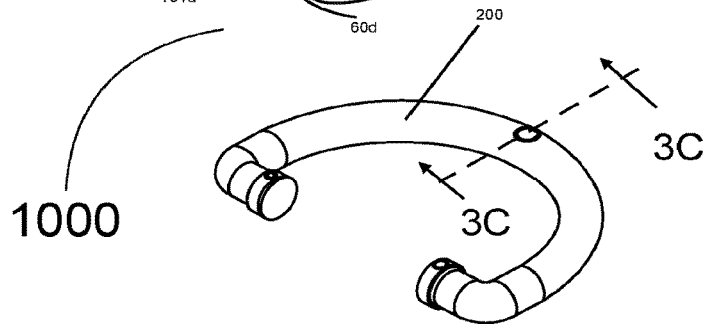
Figure 3B:
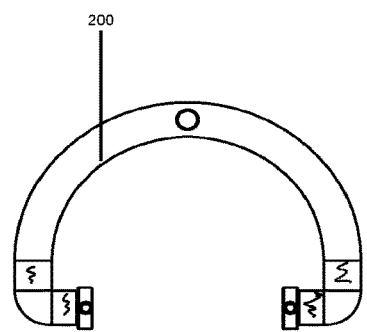
FIG. 3B illustrates a front view of the pull ring of FIG. 3A according to one example of the principles described herein.
Figure 3C:
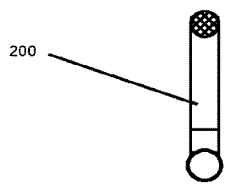
FIG. 3C illustrates a cross-sectional view of the pull ring of FIG. 3A according to one example of the principles described herein, the cross-sectional plane being cut across the dotted line of FIG. 3A.
Figure 3D:
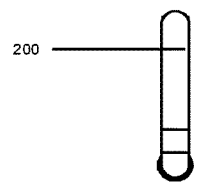
FIG. 3D illustrates a back view of the cross-section of the pull ring of FIG. 3C according to one example of the principles described herein.
Figure 3E:
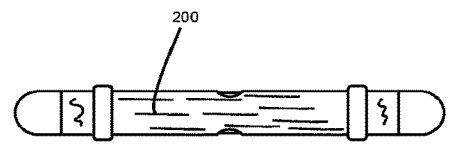
FIG. 3E illustrates a front side view of the pull ring according to one example of the principles described herein.
Figure 4A:
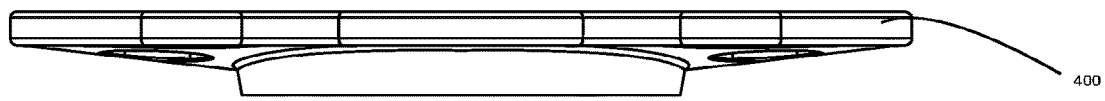
FIG. 4A illustrates a bottom view of a mouth guard according to one example of the principles described herein.
Figure 4B:
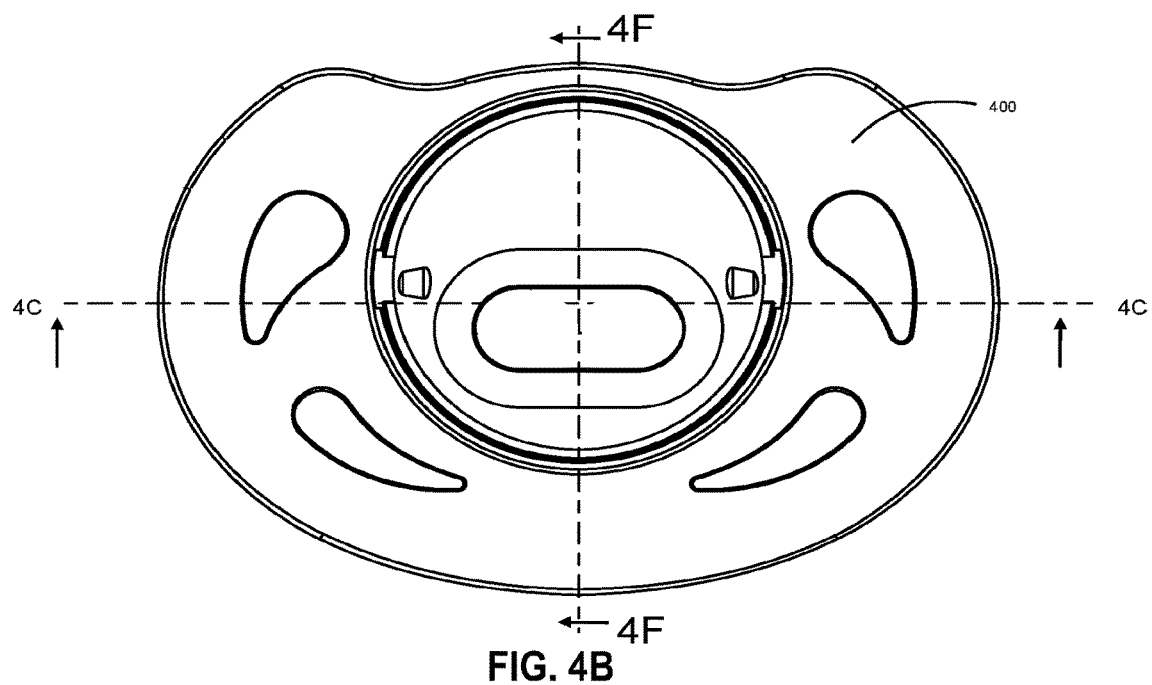
FIG. 4B illustrates a front view of the mouth guard embodiment of FIG. 4A according to one example of the principles described herein.
Figure 4C:
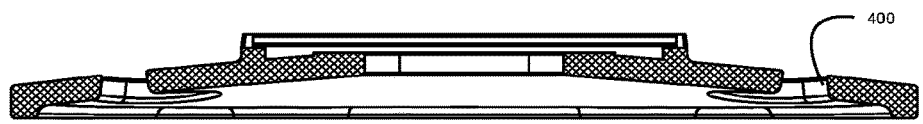
FIG. 4C illustrates a cross-sectional view of the mouth guard embodiment of FIG. 4B according to one example of the principles described herein.
Figure 4D:
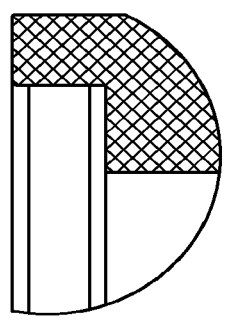
FIG. 4D illustrates an enlargement of the section that is encircled by a dotted line in FIG. 4F.
Figure 4E:
FIG. 4E illustrates a side view of an embodiment of the mouth guard according to one example of the principles described herein; the view was generated by rotating 90 degrees, towards a viewer, the right edge of the mouth guard shown in FIG. 4B.
Figure 4F:
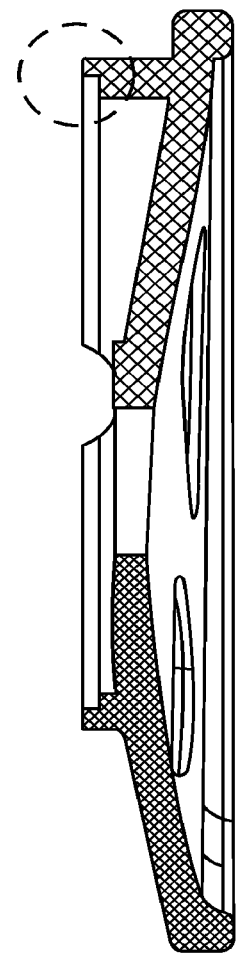
FIG. 4F illustrates a cross-sectional view of the mouth guard embodiment of FIG. 4B according to one example of the principles described herein.

Referring to FIG. 1D, at least three flexible locking hooks 174a, 174b, 174c may be coupled to the inner face 156. FIG. 1C depicts how in the preferred embodiments, an outer flange 180 of the inner cartridge structure 154 may be positioned as show in FIG. 1D and moved along axis 1001. Each of the at least three flexible locking hooks, 174a, 174b, 174c may be substantially undetachably mated with an outer flange 180 of the inner cartridge structure 154 such that a lower edge of the hooking flange, such as 1741a may be moved towards the rim of the inner cartridge structure 154 as the outer flange 180 is pressed against the hooking flange 1741a, (see FIG. 1C), and toward the inner face of the outer cartridge structure 152, sliding up and behind the flexible locking hook 174a so as to be locked into place such that any portion of inner face of the outer flange 180 coupled to the one of the flexible flocking hooks 174a, 174b, 174c is held in place by a hooking flange, such as 1741a. See FIG. 1B for a frontal perspective view of an inner cartridge structure 154 coupled to the outer cartridge structure 152 to form a cartridge assembly 150. Referring to FIG. 1B, in the preferred embodiments, the housing 300 is coupled to the mouth guard 400 at flange 3000 of mouth guard 400 via at least one type of weld selected from the group consisting of a hermetic seal, an ultrasonic weld, and a labyrinth seal. Referring to FIG. 2C, an exploded view of an embodiment is shown. Starting from the left, an outer cartridge structure 152 and inner cartridge structure 154 are shown; when coupled together, the outer cartridge structure 152 and inner cartridge structure 154 form a cartridge assembly 150 which may be inserted into housing 300; pull ring 200 may be coupled to housing 300; housing 300 may also be coupled to mouth guard 400; nipple 600 may also be coupled to housing 300 and mouth guard 400.

Referring to 5D, energy director 701 is depicted; In the preferred embodiments, the radius of the energy director 701 is 0.002 inches or less. Teeth are show in FIG. 5d, and the angle of portion 702 and the main surface of the outer cartridge structure may be between 40 and 50 degrees, 50 and 60 degrees, 63 and 66 degrees, 66 and 69 degrees, 69 and 72 degrees, 72 and 75 degrees, 75 and 79 degrees, 79 and 82 degrees, 82 and 85 degrees, 85 and 89 degrees, 89 and 92 degrees 92 and 97 degrees, 97 and 101 degrees, 101 and 107 degrees, 107 and 112 degrees, 112 and 120 degrees, 120 and 130 degrees, 130 and 170 degrees.

Figure 5A:
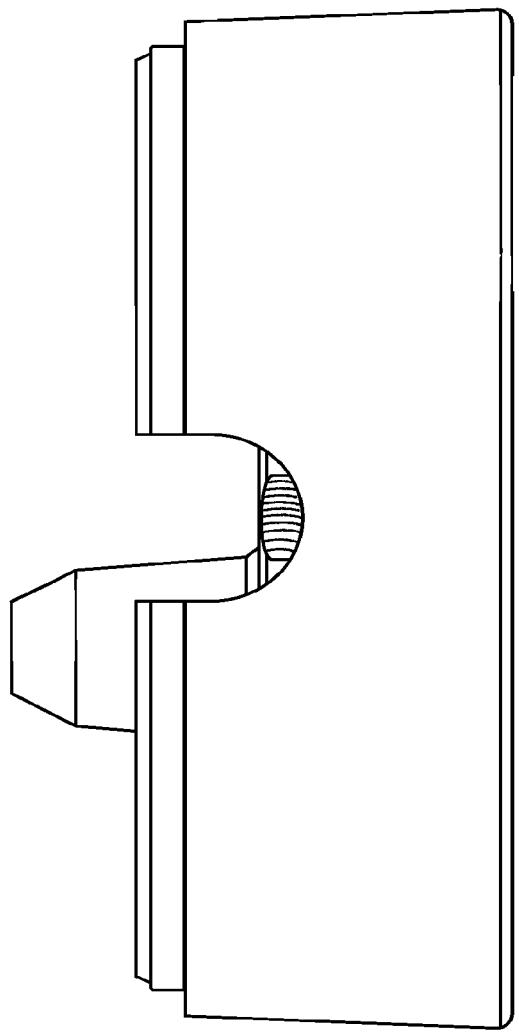
FIG. 5A depicts a side view of the housing according to one example of the principles described herein. (The view of the embodiment of the opposite side of the housing is not shown but is a mirror image of FIG. 5A.)
Figure 5B:
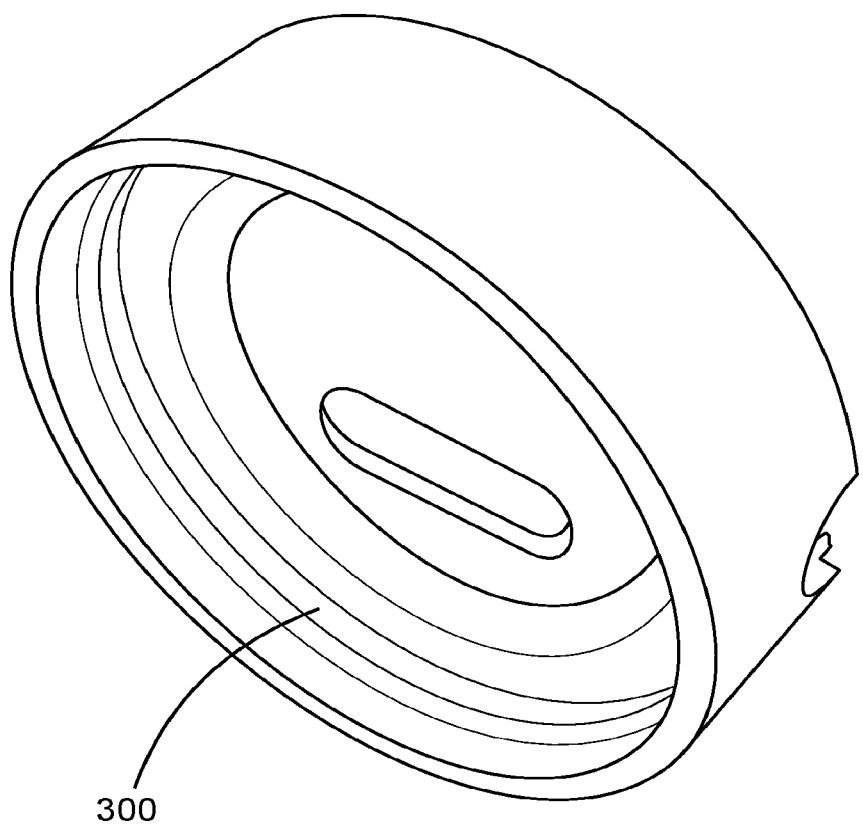
FIG. 5B illustrates a perspective view, looking down and from the front, of the housing of FIG. 5A, according to one example of the principles described herein. An embodiment of the front face of the housing is shown.
Figure 5C:
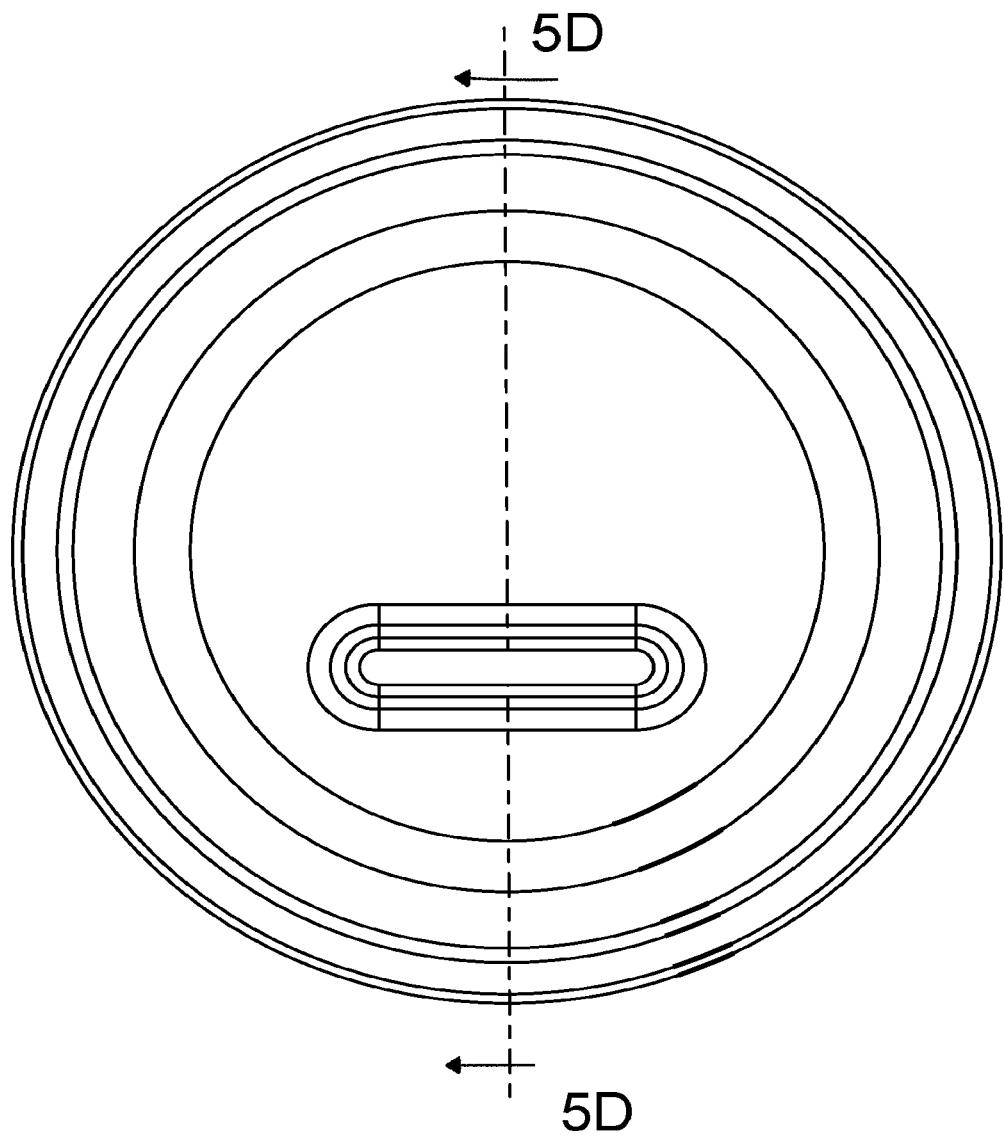
FIG. 5C illustrates a front view of the housing of FIG. 5B according to one example of the principles described herein.
Figure 5D:
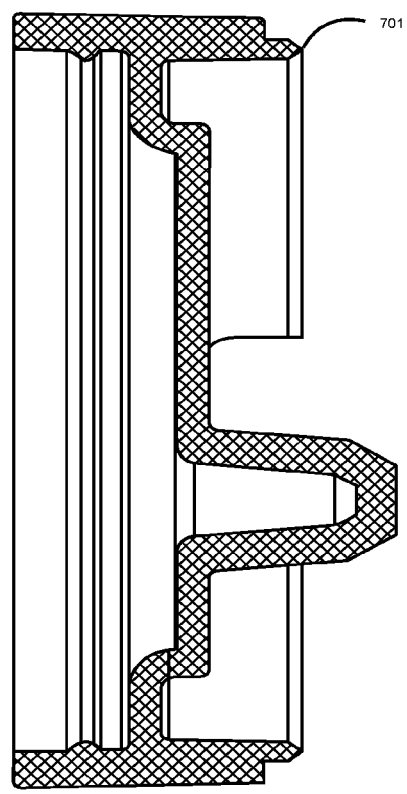
FIG. 5D illustrates a cross-sectional view of the embodiment shown in FIG. 5C, according to one example of the principles described herein; the plane is cut across the dotted line in 5D.
Figure 5E:
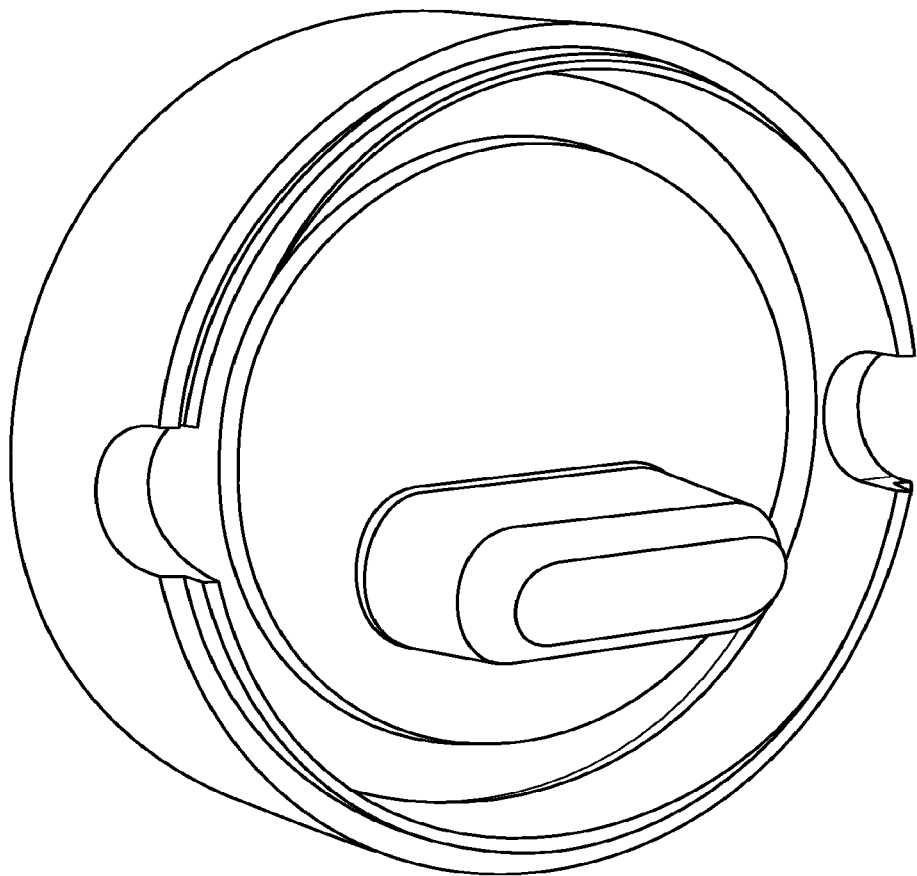
FIG. 5E illustrates a bottom-back perspective view of the back side of the housing according to one example of the principles described herein.
Figure 5F:
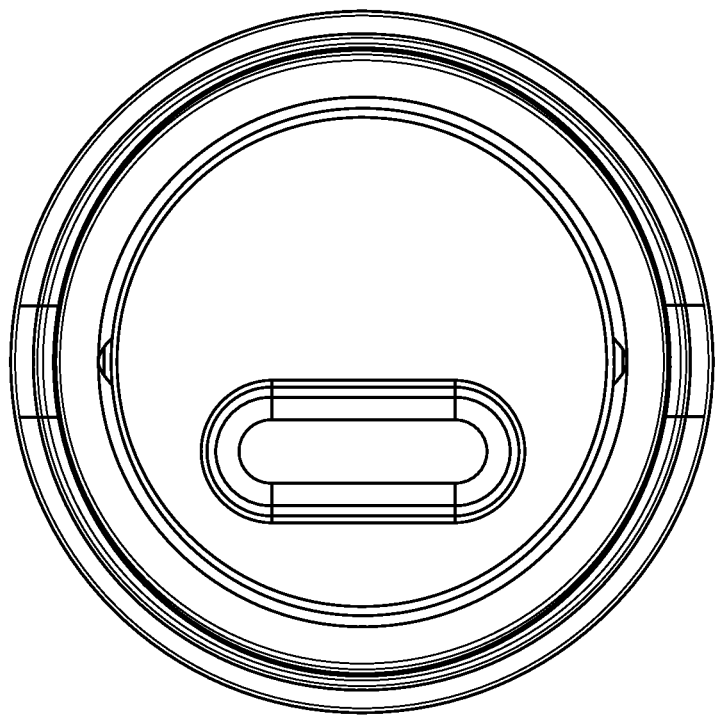
FIG. 5F illustrates a back view of the housing of FIG. 5F according to one example of the principles described herein.
Figure 8A:
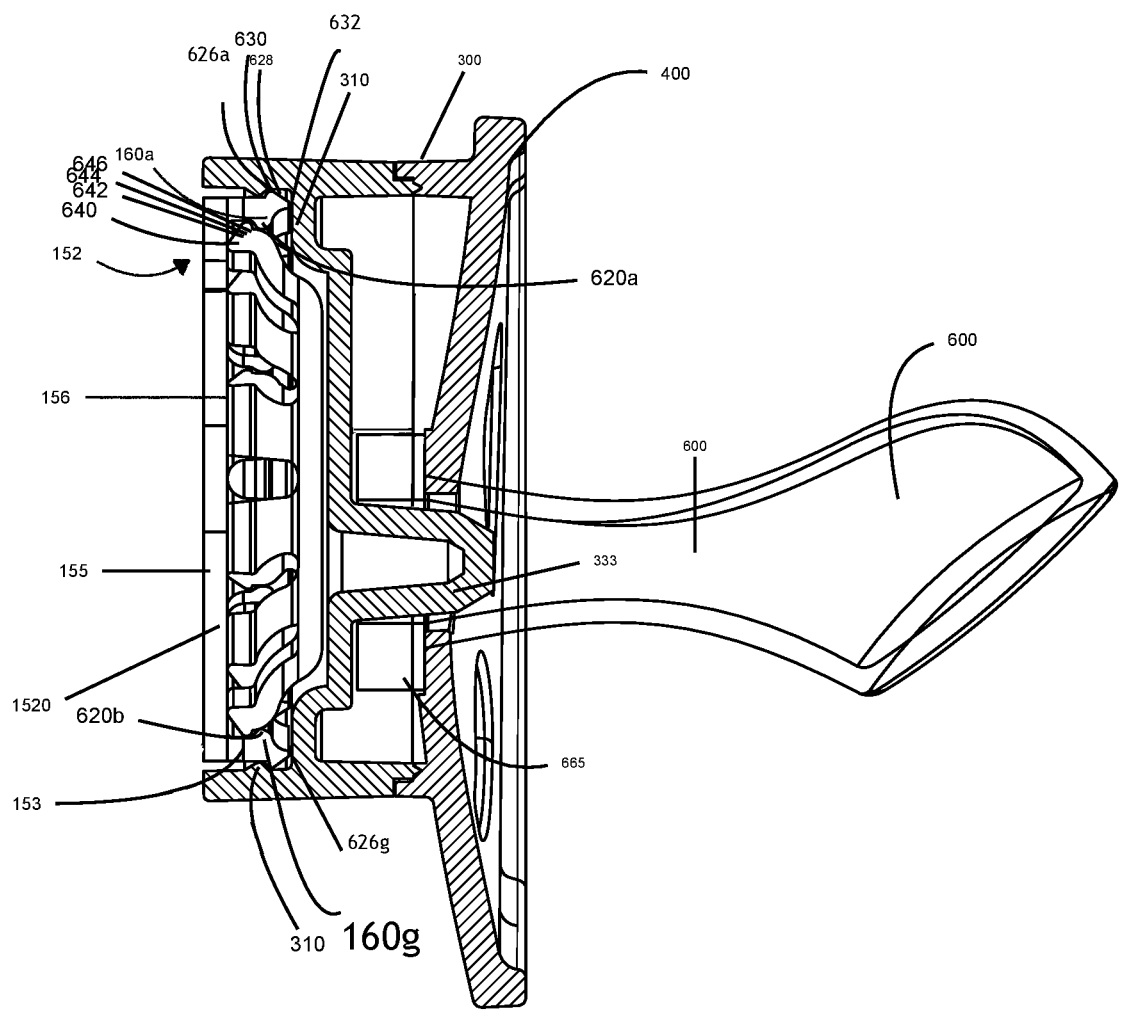
FIG. 8A depicts a cross sectional view of an embodiment of the aromatic pacifier assembly
Figure 8B:
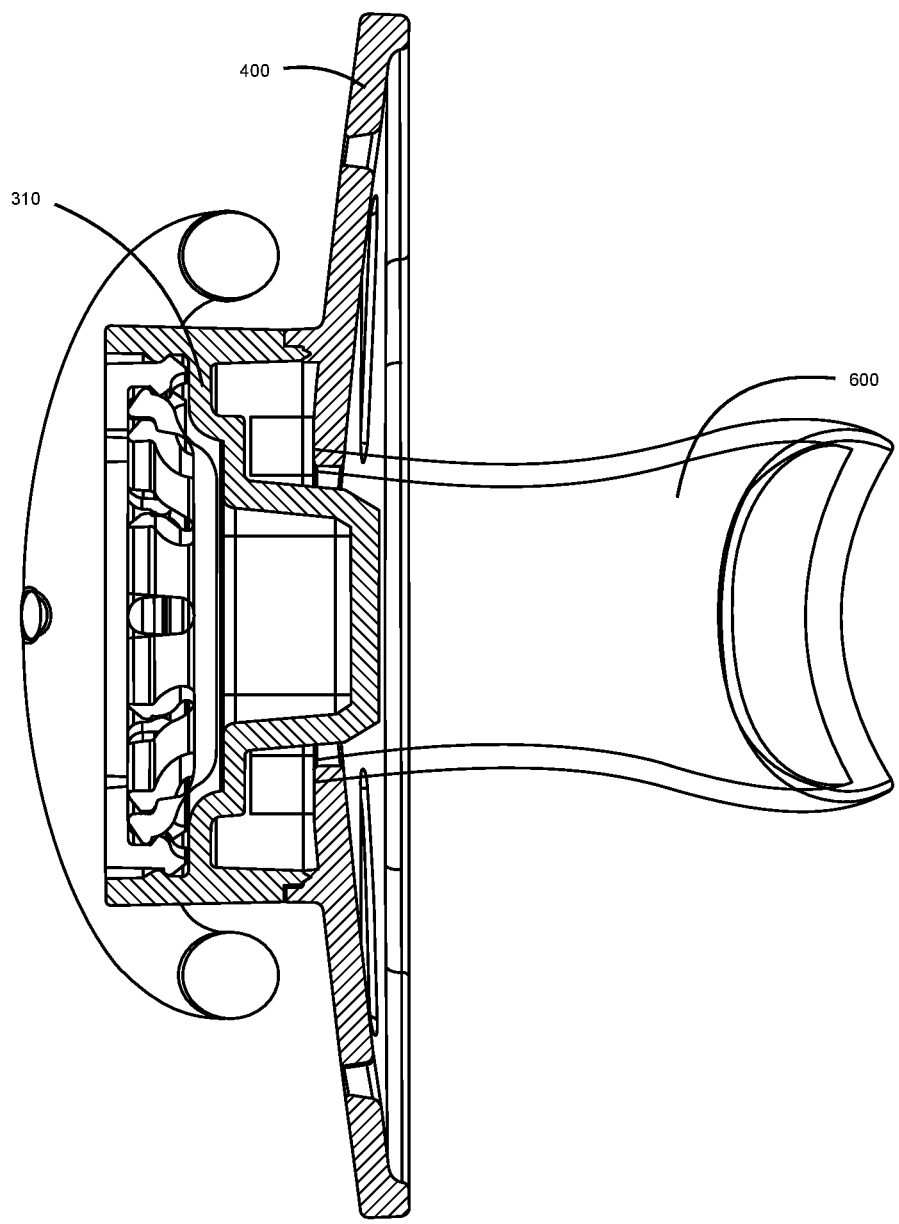
FIG. 8B depicts a cross sectional view of an embodiment of the aromatic pacifier assembly

Referring to FIG. 8A, the aromatic pacifier assembly of claim 1, may further have at least one flexible tooth of the outer cartridge structure; the housing 300 may have an annular area 310, that may circumscribe an inner face of housing 300, as shown in FIG. 5B, and, the annular area 310 may detachably mate with the tooth 160a and tooth 160g of the outer cartridge structure 152 of the cartridge assembly 150. Two locations in FIG. 8A are labeled 310 to help show the boundaries of annular area 310. In the preferred embodiments, the annular area 310 may detachably mate with a plurality of teeth 160a, 160g, etc. of the outer cartridge structure 152 of the cartridge assembly 150 since having a plurality of teeth that have been coupled to the housing so as to be disposed behind the annular area 310 may restrain the outward cartridge from being tilted at an angle so as to allow the tooth 160a to be discoupled from the annular area 310. In some embodiments there are two teeth 160a and 160g; in some embodiments there are three teeth; in the preferred embodiments there are at least 4 teeth; there may be five teeth in some embodiments, there may be six teeth in some embodiments, there may be seven teeth in some embodiments, there may be between eight and 50 teeth; in the preferred embodiments, there are 12 teeth 310a, 310b, 310c, 310d, 310e, 310f, 310g, 310h, 310i, 310j, 310k, 310l.

Figure 9A:
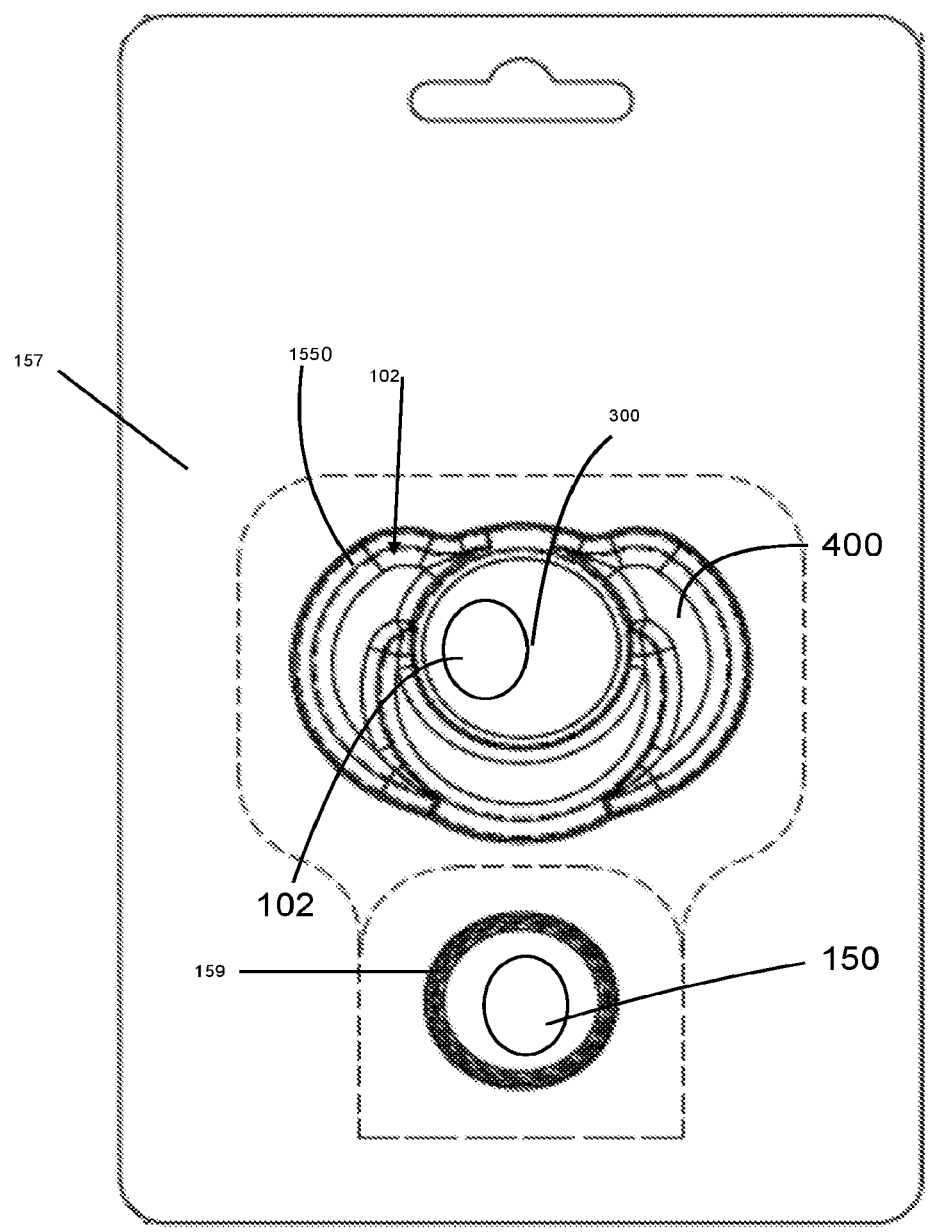
FIG. 9A depicts a front view of an embodiment of main assembly packaged in an embodiment of a first compartment and an embodiment of the cartridge assembly packaged in an embodiment of the second compartment.
Figure 9B:
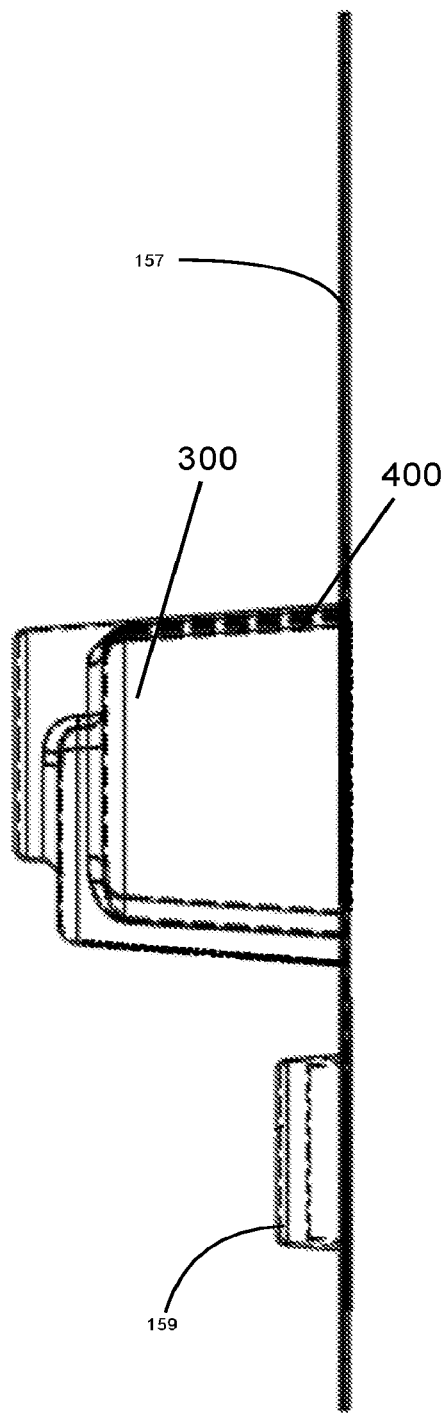
FIG. 9B depicts a side view of what is shown in FIG. 9A.
Figure 9C:
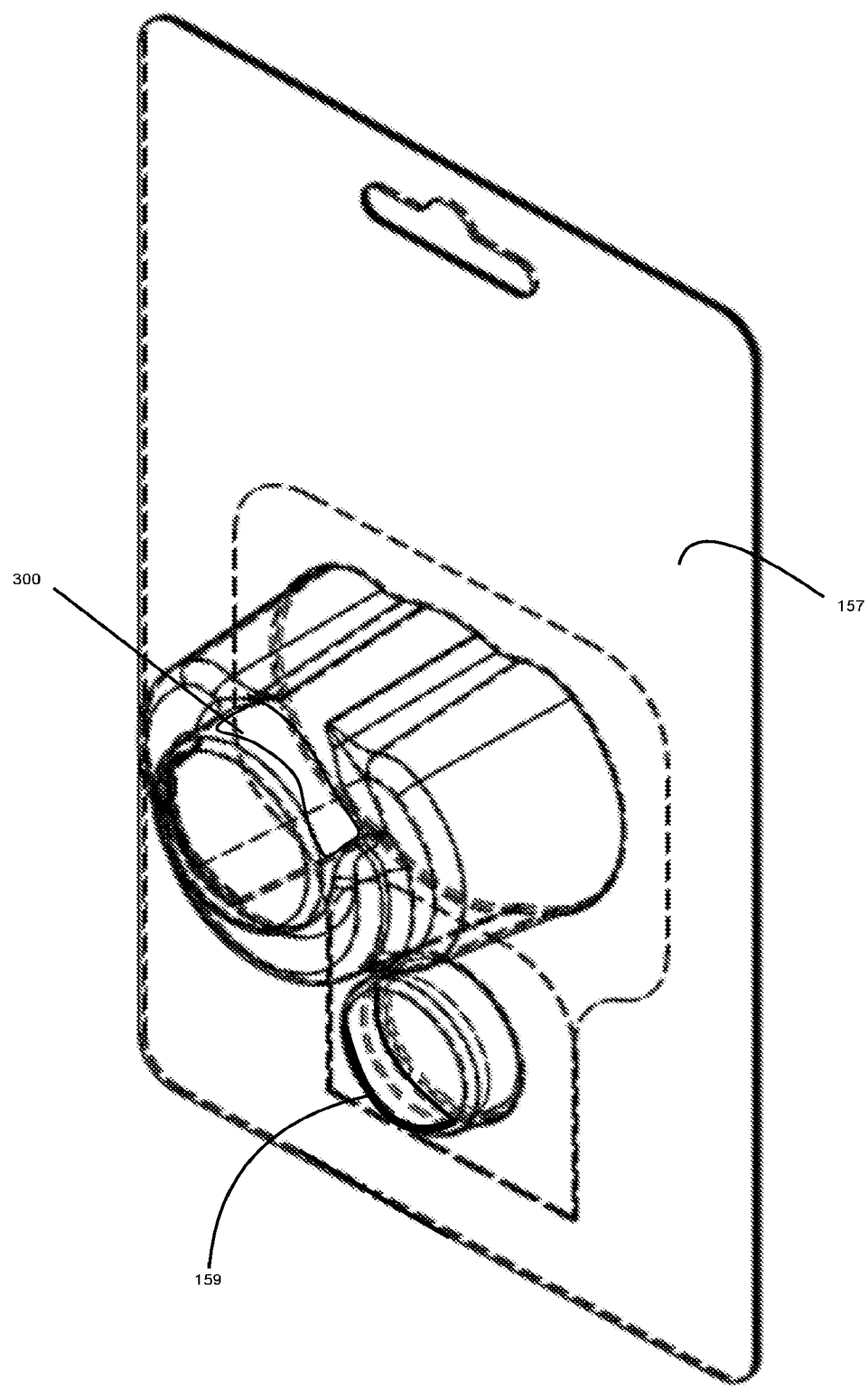
FIG. 9C depicts a perspective view of what is shown in FIG. 9A.

Referring to FIG. 9A, the aromatic pacifier assembly 101 may include two or more portions or assembled portions. The outer cartridge structure 152 may be substantially undetachably coupled to the inner cartridge structure 154, and an aromatic pad, or absorment material having aromatic compounds, may be disposed therein so as to form a cartridge assembly 150 having an aromatic pad disposed within. For purposes of the figures, the aromatic pad is shown relatively small so as to not obstruct the view of the cartridge assembly; however, in the preferred embodiments, the aromatic pad may be of any size; In the preferred embodiments, the aromatic pad is sized to fit within the cartridge assembly 150. Referring to FIG. 9A, a schematic is shown wherein the main assembly 102 is disposed in a first packaging compartment 1550, which may be plastic or see-through, coupled to a backing 157, which may have paper and may be coupled to the back edge of first packaging compartment 1550 so as to function with the first packaging compartment 1550 to keep the main assembly 102 substantially separated from an outer environment. In the preferred embodiments, the cartridge assembly 150 may be generally-aseptically disposed in a second packaging compartment 159 coupled to the backing; FIG. 9A shows a schematic for cartridge assembly 150. By packaging two or more separate compartments, the nipple may be preserved so as to avoid permeating the nipple with aromas from the absorbent material of the cartridge assembly.

Figure 6A:
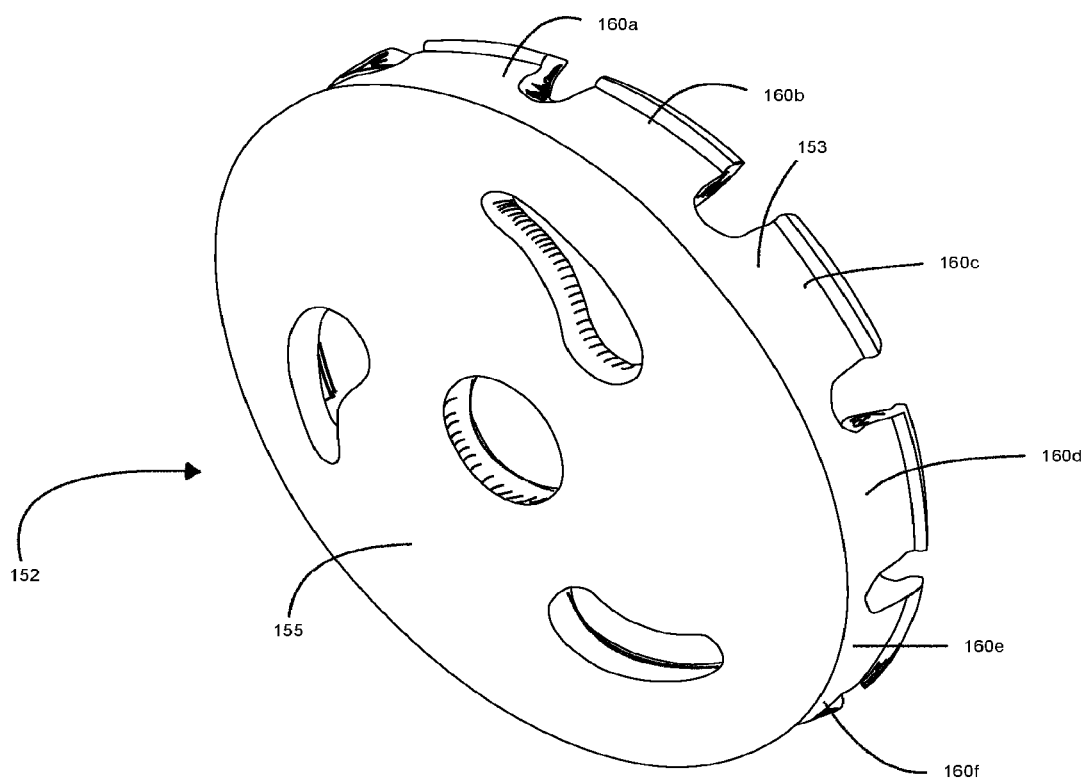
FIG. 6A illustrates a front, perspective view of an outer cartridge structure, according to one example of the principles described herein.
Figure 6B:
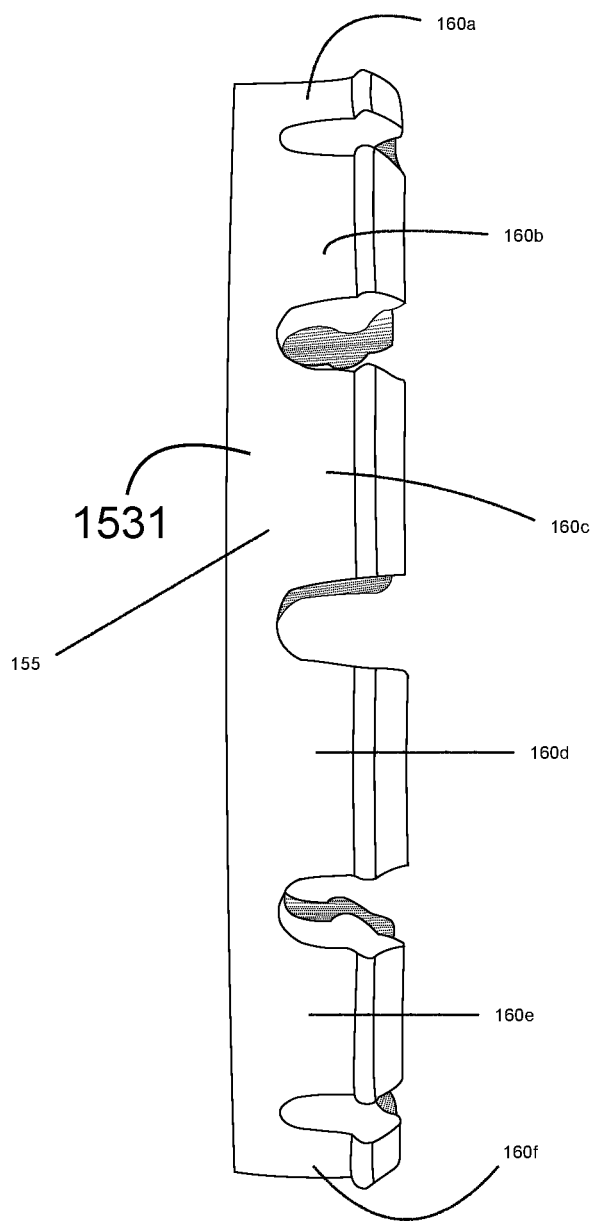
FIG. 6B illustrates a side view of the outer cartridge structure as shown in FIG. 6A, according to one example of the principles descried therein.
Figure 6C:
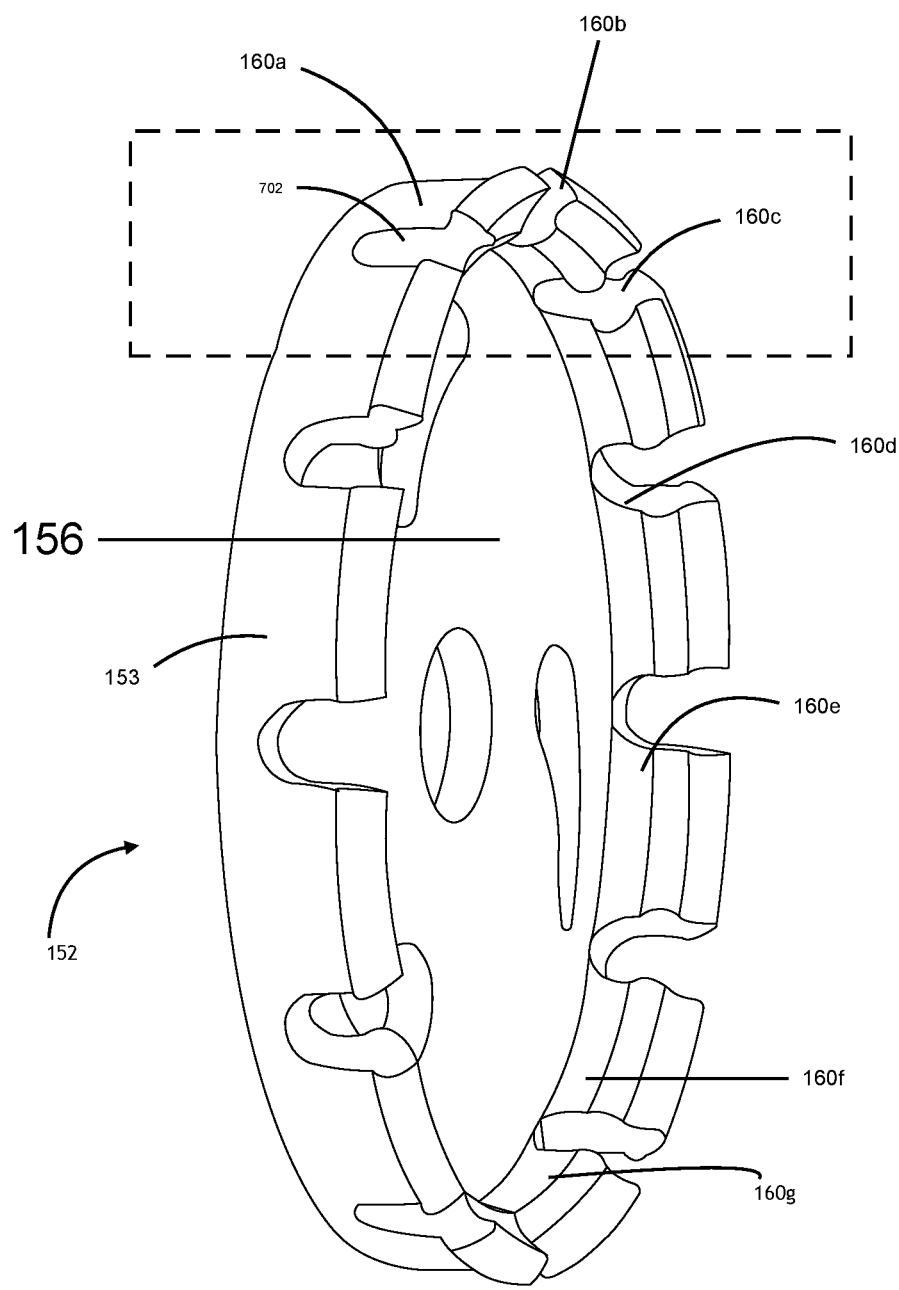
FIG. 6C illustrates a back perspective view of the outer cartridge structure as shown in FIG. 6A, according to one example of the principles descried therein.
Figure 6D:
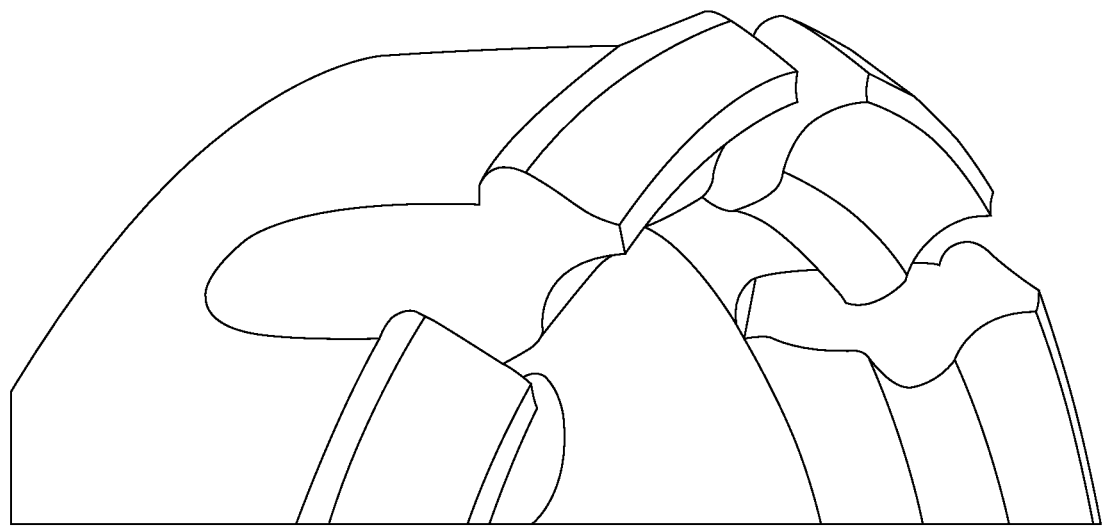
FIG. 6D illustrates a closeup of the embodiment show in in FIG. 6C; the dotted rectangle in FIG. 6C shows what is enlarged.
Figure 6E:
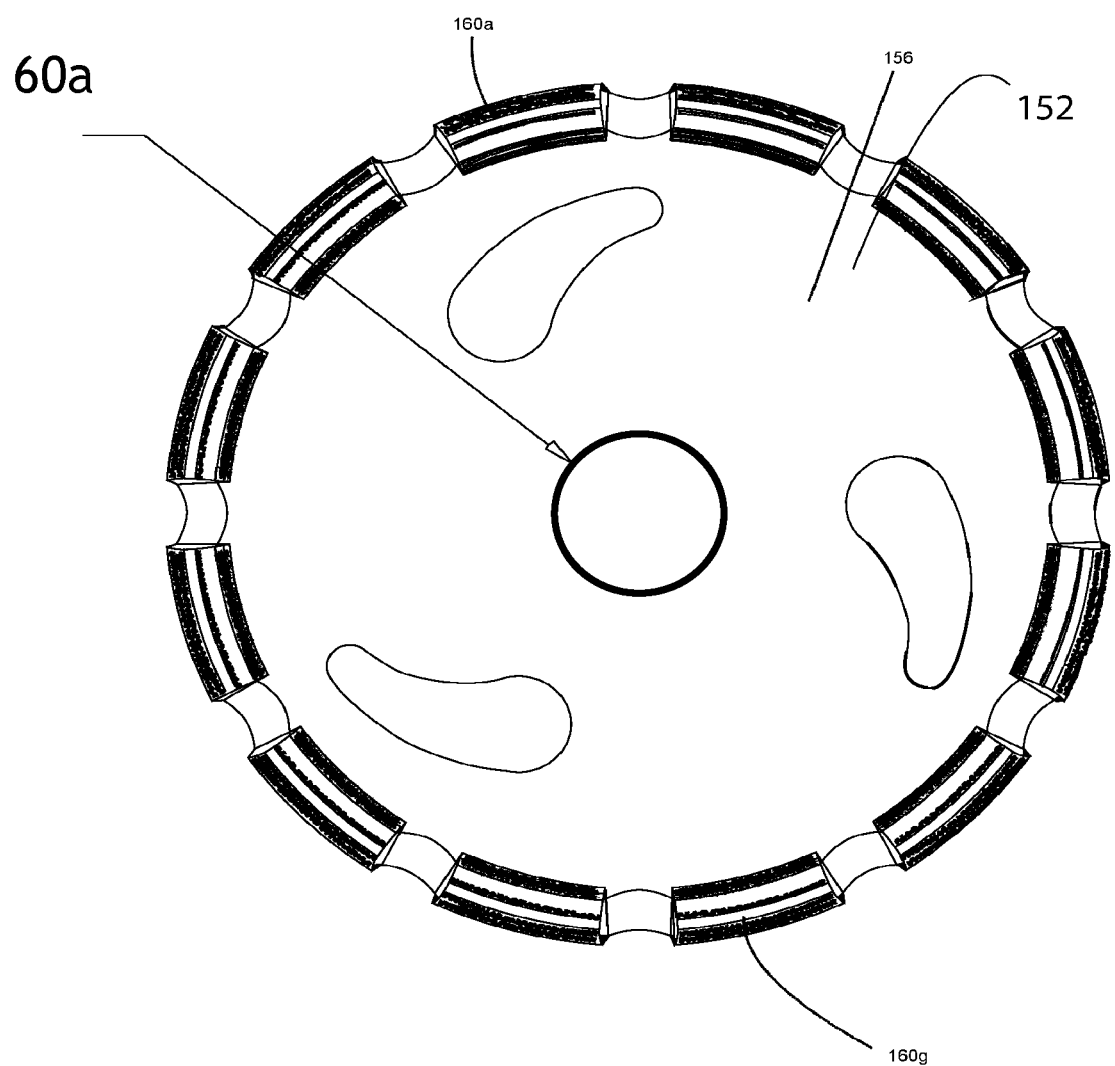
FIG. 6E illustrates a back view of the outer cartridge according to one example of the principles described herein.

Referring to FIGS. 6A and 1B, the aromatic pacifier assembly 101 may have an outer cartridge structure 152, and the outer cartridge structure 152, may further include: an outer rim lip 153, an outer face 155 (see both FIG. 6a and FIG. 6b), and an inner face 156 (shown in FIG. 6C). In the preferred embodiments, the outer cartridge structure 152 may further have a first tooth 160a and a second tooth 160g collectively disposed on an outer flange 1531 (See FIG. 6B) of the outer rim lip 153; the outer rim lip 153 may include both the outer flange 1531 and the outer rim lip 153; both the outer rim lip 153 and the outer flange 1531 may have a circumference that may be substantially similar or identical to the circumference of the outer face 155 of the outer cartridge structure 152, the inner cartridge structure 154 may have at least one tooth of the inner cartridge structure; the at least one tooth of the inner cartridge structure may have a first tooth 1541a and a second tooth 1541b of the inner cartridge structure 154; wherein the housing 300 may have an annular area 310 generally circumscribing the housing 300, wherein the first tooth 160a of the outer cartridge structure 152 may be frictionally coupled to the annular area 310 of the housing 300, the first tooth 1541a of the inner cartridge structure 154 may be frictionally coupled with the first tooth 160a of the outer cartridge structure 152, wherein the first tooth 160a of the outer cartridge structure 152 may be simultaneously and undetachably coupled to the annular area 310 of the housing 300 and to the first tooth 1541a of the inner cartridge structure 154 when the first tooth 160a of the outer cartridge structure 152 is disposed between the annular area 310 of the housing 300 and the first tooth 1541a of the inner cartridge structure.

Referring to FIG. 6C, the aromatic pacifier assembly 101 of claim 1 may include an outer cartridge structure 152 which in preferred embodiment is elliptically-shaped; the outer cartridge structure 152 may further have an outer rim lip 153, wherein the outer rim lip 153 has a flexible first tooth 160a, a flexible second tooth 160g, a flexible third tooth 160c, a flexible fourth tooth 160d, a flexible fifth tooth 160e, a flexible sixth tooth 160f, and a flexible seventh tooth 160b; each of the seven teeth may further have parts like the parts on 160a such as an inward-facing, generally convex ridge 620; and a tip 622 that may have a concave edge 624 adjacent to the ridge 620, a generally planar edge 626 adjacent to the concave edge 624, a beveled edge 628 adjacent to the generally planar edge 626, a generally concave outer edge 630 adjacent to the beveled edge 628, a portion 632 receiving the annular area 310 of the housing 300; portion 632 (and corresponding portions for the plurality of tooth) may be frictionally and undetachably coupled to the annular area 310 of the housing 300 when each of the seven teeth 160a, 160g,160c,160d,160e,160f,160b of the outer cartridge structure are undetachably and frictionally disposed between the annular area of the housing 300 and a number of teeth 1541a, 1541b, 1541c, 1541d, 1541e, 1541f, 1541g, of the inner cartridge structure.

Referring to FIG. 1D, a vent area 60a is disclosed and it may be elliptical or circular. The aromatic pacifier assembly 101 may include vent area 61a, which may be comma-shaped, which may refer to having a first end that is elliptical or circular, having a first diameter, and a second end that may be circular with a smaller diameter than the first end, and having a first curved line that is tangent to both the first end and the second end, and having a second curved line that may be tangent to the first end and the second end. There is no limit on the number of vent areas that may be included on the outer face of the cartridge assembly, but in preferred embodiments there are 4 vent areas: 60*a*, 61*a*, 61*b*, 61*c*.

The aromatic pacifier assembly 101 may have number of teeth 160*a*, 160*b* of the outer cartridge structure 152 which may equal the number of teeth 1541*a*, 1541*b*, 1541*c*, 1541*d*, 1541*e*, 1541*f*, 1541*g* of the inner cartridge structure. The number of teeth of the outer cartridge structure may range between 2 and 100. Preferably, the number of teeth of the outer cartridge structure 152 may be with in 5 less or 5 greater than the number of teeth of the inner cartridge structure. Preferably, the teeth of the outer cartridge structure interlock or are coupled behind the teeth of the inner cartridge structure.

The inner cartridge structure further having at least six inner cartridge teeth 1541*a*, 1541*b*, 1541*c*, 1541*d*, 1541*e*. The teeth may be wedge shaped and may be tapered so as to be flexible. The teeth may have a ridge. One or more of the teeth, but preferably all of the teeth, of the inner cartridge structure.

Figure 7A:
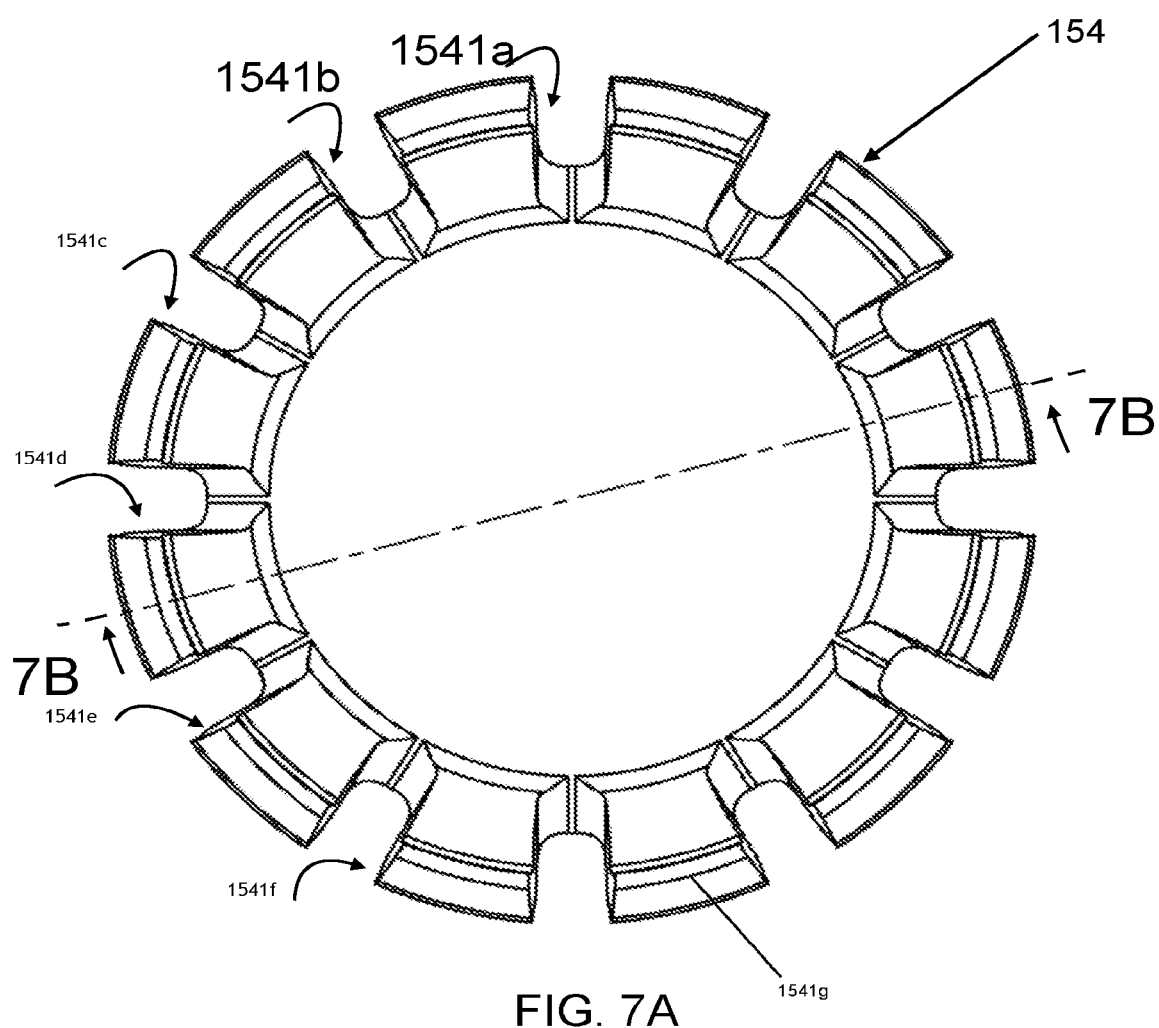
FIG. 7A illustrates a front view of an embodiment of an inner cartridge structure embodiment according to one example of the principles described herein.
Figure 7B:
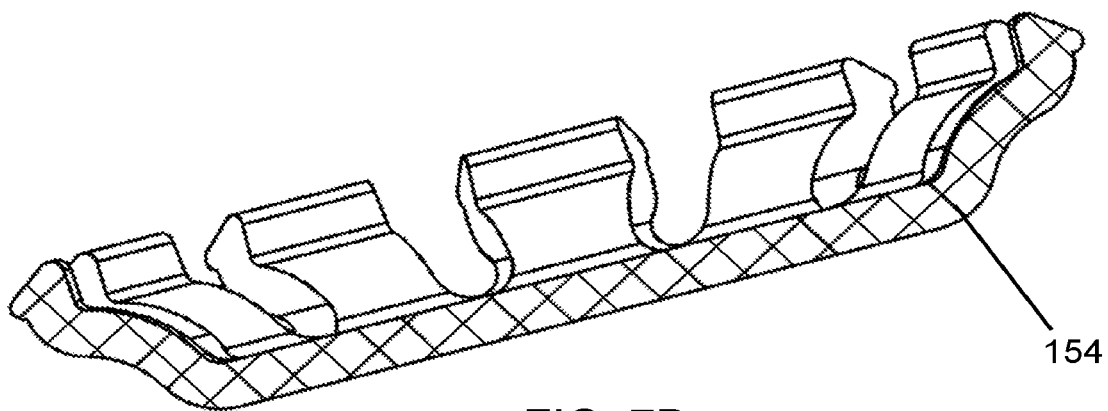
FIG. 7B illustrates a sectional perspective view of an embodiment the inner cartridge structure of FIG. 7A.
Figure 7C:
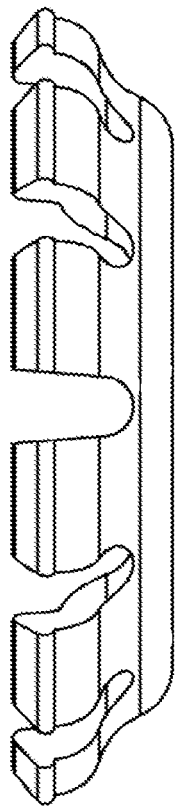
FIG. 7C illustrates a side perspective view of an embodiment of the inner cartridge structure of FIG. 7A. (The opposing side is not shown but is a mirror image of FIG. 7C.)
Figure 7D:
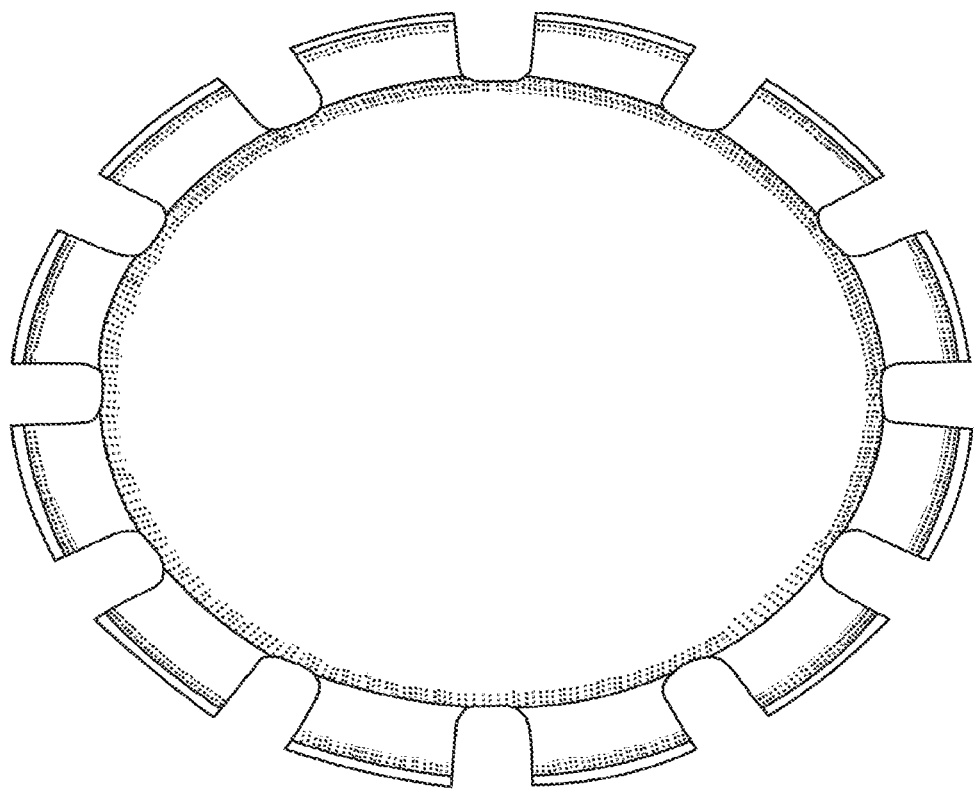
FIG. 7D illustrates a back view of the embodiment of the inner cartridge structure depicted in FIG. 7C.

Referring to FIG. 8A and FIG. 7A, each of the one or more inner cartridge teeth 1541*a*, 1541*b*, 1541*c*, 1541*d*, 1541*e*, 1541*f*, and 1541*g* may have a) a generally convex flexible tip 640, b) a beveled, outer edge 642 of the flexible tip 640 may have a flange 644, and c) an upper edge 646 of the flexible tip 640; the upper edge 646 of the flexible tip 640 may be detachably coupled with the outer cartridge structure 152, and each flange 644 of each of the outer edge 642 of the flexible tip 640 of each of the at least six inner cartridge teeth 1541*a*, 1541*b*, 1541*c*, 1541*d*, 1541*e*, 1541*f* may be coupled to and may be nested behind one of the inward-facing, generally convex ridges 620*a*, 620*g*.

Referring to FIG. 8A, the outer cartridge structure 152 may have generally planar edges, such as 626*a* and 626*g*, adjacent to the concave edges 624 of the at least seven teeth 160*a*, 160*b*, 160*c*, 160*d*, 160*e*, 160*f*, 160*g* of the outer cartridge structure 152, and the one or more planar edges 626 (referred herein as plural since each of the at least seven teeth may have a planar edge 626) may be substantially undetachably coupled to the housing 300 (substantially undetachably referring to the culmination of the different teeth that may be interlocking which may constrain the movement of a single edge or tooth from being moved at a sufficient angel so as to be detached); and, wherein each of the generally concave outer edges 630 adjacent to the beveled edges 628 of the at least seven teeth 160*a*, 160*b*, 160*c*,160*d*,160*e*,160*f*,160*g* (flexible) of the outer cartridge structure 152 may be substantially undetachably coupled to the housing 300, wherein a second generally planar edge 6262 may be substantially undetachably coupled to the housing 300.

Referring to FIG. 8A, the housing 300 may have a ledge 333, the nipple 600 may further have a collar 665 being coupled to the mouth guard 400 and being disposed upon the ledge 333 which may be generally C-shaped or the mirror image of C-shaped; wherein at least one aromatic substance is disposed upon said absorbent material 356, which may be a pad, the at least one aromatic substance selected from the group consisting of nontoxic substances, volatile substances, essential oils, aromatic compounds, lavender essential oil, orange essential oil, lemon essential oil, eucalyptus essential oil, peppermint essential oil, rosemary essential oil, almond oil essential oil, coconut oil essential oil, camphor essential oil, cedar essential oil, menthol essential oil, tea tree oil essential oil, vanilla essential oil, chamomile essential oil, and cannabis essential oil, alcohols, and combinations thereof.

Referring to FIG. 8A, the nipple may be inverted. Any of the nipples depictions in the drawings may be inverted.

Methods of use are contemplated. A method of using an aromatic pacifier assembly for providing aromatic compounds to a person is disclosed, the method having the steps of: removing an aromatic cartridge assembly, wherein an absorbent material 356 such as a pad that has been infused with essential oils or aromatic compounds may be generally engulfed by the aromatic cartridge assembly, from a first sterile compartment of a packaged product; removing a main assembly 102 having a nipple coupled to a mouthguard from a second compartment of the packaged product; sterilizing the main assembly 102 so as to sterilize the nipple; removing a sticker detachably sealed to at least one vent of the cartridge assembly; mating the cartridge assembly with the housing so as to hear a clicking sound; inserting the nipple into the mouth of a human, and allowing at least one aromatic compound to be diffusing through at least one vent of the outer cartridge structure.

The foregoing descriptions of embodiments have been presented only for purposes of illustration and description. They are not intended to be exhaustive or to limit the embodiments to the forms disclosed. Accordingly, many modifications and variations will be apparent to practitioners skilled in the art. Additionally, the above disclosure is not intended to limit the embodiments. The scope of the embodiments is defined by the appended claims.

The invention claimed is:

1. An aromatic pacifier assembly comprising
a main assembly comprising
  a nipple;
  a mouth guard;
  a housing coupled to the mouth guard; and,
  a cartridge assembly; the cartridge assembly comprising
    an outer cartridge structure, having a number of teeth of the outer cartridge structure, the number of teeth of the outer cartridge structure comprising a first tooth of the outer cartridge structure;
    an inner cartridge structure, having a number of teeth of the inner cartridge structure, the number of teeth of the inner cartridge structure comprising a first tooth of the inner cartridge structure; and,
    an absorbent material, the absorbent material having been infused with an amount of aromatic compounds; the absorbent material being disposed within the cartridge assembly; the outer cartridge structure is undetachably coupled to the inner cartridge structure; the main assembly is disposed in a first packaging compartment coupled to a backing, and the cartridge assembly is aseptically disposed in a second packaging compartment coupled to the backing.

2. An aromatic pacifier assembly comprising
a main assembly comprising
  a nipple;
  a mouth guard;
  a housing coupled to the mouth guard; and,
  a cartridge assembly; the cartridge assembly comprising an outer cartridge structure, having a number of teeth of the outer cartridge structure, the number of teeth of the outer cartridge structure comprising a first tooth of the outer cartridge structure;

an inner cartridge structure, having a number of teeth of the inner cartridge structure, the number of teeth of the inner cartridge structure comprising a first tooth of the inner cartridge structure; and, an absorbent material, the absorbent material having been infused with an amount of aromatic compounds; the absorbent material being disposed within the cartridge assembly; wherein the housing comprises an annular area; the annular area undetachably mating with the number of teeth of the outer cartridge structure of the cartridge assembly, wherein the first tooth of the outer cartridge structure is simultaneously and undetachably coupled to the annular area of the housing.

3. An aromatic pacifier assembly comprising a main assembly comprising
- a nipple;
- a mouth guard;
- a housing coupled to the mouth guard; and, a cartridge assembly; the cartridge assembly comprising
an outer cartridge structure, having a number of teeth of the outer cartridge structure, the number of teeth of the outer cartridge structure comprising a first tooth of the outer cartridge structure;

wherein the outer cartridge structure further comprises
an outer rim lip, having an outer flange;
an outer face; and,
an inner face;

an inner cartridge structure, having a number of teeth of the inner cartridge structure, the number of teeth of the inner cartridge structure comprising a first tooth of the inner cartridge structure; and, an absorbent material, the absorbent material having been infused with an amount of aromatic compounds; the absorbent material being disposed within the cartridge assembly;

the number of teeth of the outer cartridge structure further comprises a second tooth of the outer cartridge structure; the first tooth of the outer cartridge structure and the second tooth of the outer cartridge structure are collectively disposed on an outer flange of the outer rim lip; the number of teeth of the inner cartridge structure further comprises a second tooth of the inner cartridge structure;

the housing comprises an annular area circumscribing the housing; the first tooth of the outer cartridge structure is frictionally coupled to the annular area of the housing; the first tooth of the inner cartridge structure is frictionally coupled to the first tooth of the outer cartridge structure; the first tooth of the outer cartridge structure is simultaneously and undetachably coupled to the annular area of the housing and to the first tooth of the inner cartridge structure when the first tooth of the outer cartridge structure is disposed between the annular area of the housing and the first tooth of the inner cartridge structure.

\* \* \* \* \*